United States Patent [19]

Adams, Jr.

[11] 4,425,153

[45] Jan. 10, 1984

[54] HERBICIDAL SULFONAMIDES

[75] Inventor: John B. Adams, Jr., Hockessin, Del.

[73] Assignee: E. I. Du Pont de Nemours & Co., Wilmington, Del.

[21] Appl. No.: 340,301

[22] Filed: Jan. 18, 1982

Related U.S. Application Data

[63] Continuation of Ser. No. 168,353, Jul. 11, 1980, abandoned.

[51] Int. Cl.$^3$ ............... A01N 43/54; A01N 43/66
[52] U.S. Cl. ............................................. 71/92; 71/93; 544/211; 544/253; 544/278; 544/321; 544/332
[58] Field of Search ................ 71/92, 93; 544/211, 544/253, 278, 321, 332

[56] References Cited

U.S. PATENT DOCUMENTS 4,238,621 12/1980 Levitt .................................... 71/92
4,342,587 8/1982 Levitt .................................... 71/92

Primary Examiner—Paul M. Coughlan, Jr

[57] ABSTRACT

This invention relates to ortho(acyloxy)benzenesulfonamides and their use as herbicides.

22 Claims, No Drawings

HERBICIDAL SULFONAMIDES

This is a continuation, of application Ser. No. 168,353, filed July 11, 1980, now abandoned.

BACKGROUND OF THE INVENTION

This invention relates to ortho(acyloxy)benzenesulfonamides and their use as herbicides.

Netherlands Pat. No. 121,788, published Sept. 15, 1966, teaches the preparation of compounds of Formula (I) and their use as general or selective herbicides:

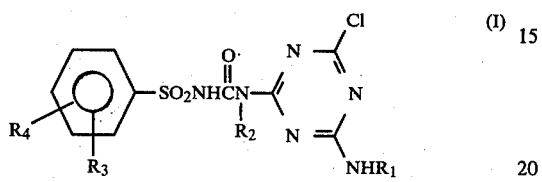

wherein
$R_1$ and $R_2$ may independently be alkyl of 1–4 carbon atoms; and
$R_3$ and $R_4$ may independently be hydrogen, chlorine or alkyl of 1–4 carbon atoms.

Compounds of Formula (II), and their use as antidiabetic agents, are reported in *J. Drug. Res.* 6, 123 (1974):

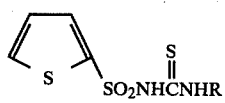

wherein R is pyridyl.

In U.S. Pat. No. 4,127,405, compounds are disclosed of the general formula:

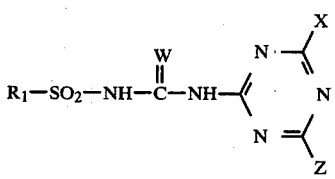

wherein
$R_1$ is

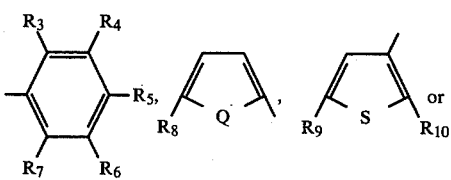

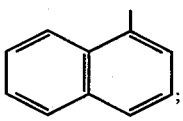

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;
$R_5$ is hydrogen, fluorine, chlorine, bromine, methyl or methoxy;
$R_7$ is hydrogen, fluorine, chlorine, bromine, alkyl of 1–2 carbon atoms or alkoxy of 1–2 carbon atoms;
$R_8$ is hydrogen, methyl, chlorine or bromine;
$R_9$ and $R_{10}$ are independently hydrogen, methyl, chlorine or bromine;
W and Q are independently oxygen or sulfur;
n is 0, 1 or 2;
X is hydrogen, chlorine, bromine, methyl, ethyl, alkoxy of 1–3 carbon atoms, trifluoromethyl, $CH_3S$— or $CH_3OCH_2$—; and
Z is methyl or methoxy; or their agriculturally suitable salts; provided that:
(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;
(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and
(c) when $R_3$ and $R_7$ are both hydrogen, at least one of $R_4$, $R_5$ and $R_6$ must be hydrogen.

In particular, the patent discloses orthosubstituted compounds wherein the substitution is $C_1$–$C_4$ alkyl.

The presence of undesired vegetation causes substantial damage to useful crops, especially agricultural products that satisfy man's basic food needs, such as soybeans, corn, wheat and the like. The current population explosion and concomitant world food shortage demand improvements in the efficiency of producing these crops. Preventing or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. However, the need exists for still more effective herbicides that destroy or retard weeds without causing significant damage to useful crops.

SUMMARY OF THE INVENTION

This invention relates to novel compounds of Formula I, to compositions containing them, and to their method of use as herbicides having both pre- and post-emergence activity:

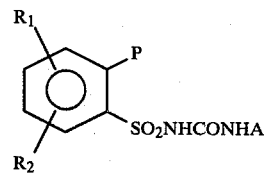

wherein
P is

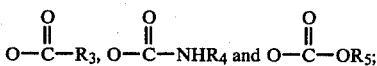

$R_1$ is H, F, Cl, Br, $C_1$–$C_3$ alkyl, $NO_2$, $C_1$–$C_3$ alkoxy, $CF_3$ or

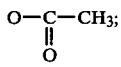

$R_2$ is H, CH$_3$ or Cl;

$R_3$ is H; C$_1$–C$_5$ alkyl; C$_2$–C$_3$ alkenyl; C$_2$–C$_3$ alkynyl; C$_1$–C$_4$ alkyl substituted with 1–3 substituents selected from 0–3 F, 0–3 Cl, 0–3 Br, and OCH$_3$; C$_2$–C$_3$ alkenyl substituted with Cl; C$_3$–C$_6$ cycloalkyl; or

$R_4$ is C$_1$–C$_6$ alkyl; C$_3$–C$_4$ alkenyl; C$_3$–C$_6$ cycloalkyl; C$_5$–C$_6$ cycloalkyl substituted with CH$_3$;

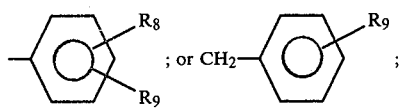

$R_5$ is C$_1$–C$_6$ alkyl or

$R_6$ and $R_7$ are independently H, NO$_2$, CH$_3$, Cl or OCH$_3$;

$R_8$ is H, F, Cl, Br, C$_1$–C$_3$ alkyl, NO$_2$, CN, SO$_2$CH$_3$, OCH$_3$, SCH$_3$ or CF$_3$;

$R_9$ is H or C$_1$–C$_3$ alkyl;

$R_{10}$ is H, CH$_3$ or Cl;

A is

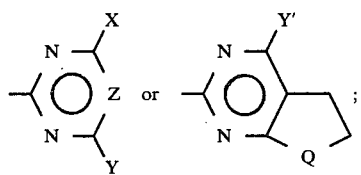

X is H, Cl, Br, CH$_3$, CH$_3$CH$_2$, C$_1$–C$_3$ alkoxy, CF$_3$, CH$_3$S or CH$_3$OCH$_2$;

Y is CH$_3$ or CH$_3$O;

Z is N, CH, C—Cl, C—BR, C—CN, C—CH$_3$, —C—CH$_2$CH$_3$, C—CH$_2$CH$_2$Cl or C—CH$_2$CH=CH$_2$;

Y' is H, CH$_3$, OCH$_3$ or Cl; and

Q is O or CH$_2$;

and their agriculturally suitable salts.

Preferred in increasing order and for reasons of higher activity and/or lower cost and/or greater ease of synthesis are those compounds of:

(1) The generic scope where Z is N, CH, C—Cl, C—CN, C—Br or C—CH$_3$;

(2) Preferred 1 where Z is CH or N and X is CH$_3$ or OCH$_3$;

(3) Preferred 2 where A is

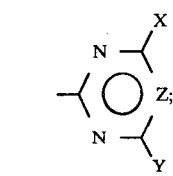

(4) Preferred 3 where $R_1$ is H;

(5) Preferred 4 where $R_2$ is H; and (6) Preferred 5 where $R_3$, $R_4$ and $R_5$ are C$_1$–C$_3$ alkyl.

Specifically preferred for reasons of highest herbicidal activity and/or lowest cost and/or greatest ease in synthesis are:

3,5-dichloro-N-[(4,6-dimethoxypyrimidin-2-yl)aminocarbonyl]-2-hydroxybenzenesulfonamide; and 3,5-dichloro-2-hydroxy-N-[(4-methoxy-6-methylpyrimidin-2-yl)aminocarbonyl)benzenesulfonamide.

The following compounds of Formula II are novel and useful as intermediates in the preparation of the herbicides of this invention.

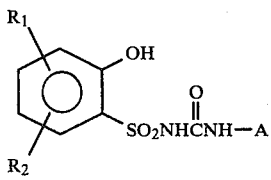

Synthesis

Compounds of Formula I can be made by one of the methods (1 or 2) shown below, depending on the identity of group P:

Method 1

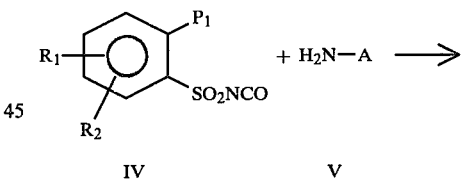

VI (compound I, wherein group P is limited to P$_1$)

wherein P$_1$ is

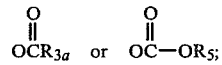

$R_{3a}$ is H; C$_1$–C$_5$ alkyl; C$_1$–C$_4$ alkyl substituted with 1–3 substituents selected from 0–3 F, 0–3 Cl, 0–3 Br and OCH$_3$; C$_4$–C$_6$ cycloalkyl; or

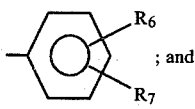

A, $R_1$, $R_2$, $R_5$, $R_6$ and $R_7$ are as defined in Formula I.

The reaction is best carried out in inert aprotic organic solvents such as methylene chloride, tetrahydrofuran or acetonitrile, at ambient pressure and temperatures from 0° to 80° C. The mode of addition is not critical; however, it is preferred to add the aminoheterocycle to a stirred solution of the sulfonyl isocyanate, thereby lessening the chance of reaction between the aminoheterocycle and group P.

The reaction is generally exothermic. In some cases, the desired product is insoluble in the reaction medium and crystallizes from it in pure form. Products soluble in the reaction mixture are isolated by evaporation of the solvent, trituration of the residue with solvents in which it is sparingly soluble, such as 1-chlorobutane, ethyl ether or pentane, and filtration.

The intermediate sulfonyl isocyanates of Formula IV can be prepared from the parent sulfonamides of Formula VII as shown in Equation 1b. Reaction with phosgene in the pressure of n-butyl isocyanate and a catalytic amount of 1,4-diaza[2.2.2]bicyclooctane (DABCO) at reflux in a solvent such as chlorobenzene or xylenes, according to the procedure of H. Ulrich and A. A. Y. Sayigh, *Newer Methods of Preparative Organic Chemistry*, Vol. VI, p. 223-241, Acadamic Press, New York and London, W. Foerst, Ed., affords the sulfonyl isocyanates IV.

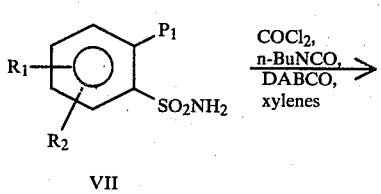

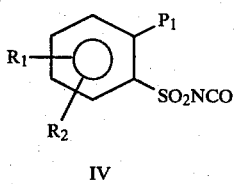

A mixture of the appropriate sulfonamide VII, an alkyl isocyanate such as butyl isocyanate and a catalytic amount of 1,4-diaza[2.2.2]bicyclooctane (DABCO) in xylene, chlorobenzene or other inert solvent of sufficiently high boiling point (e.g. ≧135°) is heated to approximately 135°. Phosgene is added to the mixture until an excess of phosgene is present as indicated by a drop in the boiling point. The mixture is heated further to drive off excess phosgene. The mixture is cooled and filtered to remove insoluble by-products under a dry stream of nitrogen or air. The solvent and alkyl isocyanate are distilled off in vacuo leaving a residue which is the crude sulfonyl isocyanate IV. Alternatively, the sulfonyl isocyanate can be made by the method of Ulrich, et al., J. Org. Chem. 34, 3200 (1969), as described after Equation 2b.

Sulfonamides of Formula VII can be prepared by several different methods known in the literature. o-Hydroxybenzenesulfonamides of Formula VIII can be reacted with an appropriate reagent E [an acyl halide or anhydride, i.e.,

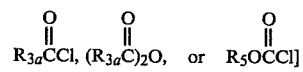

as shown in Equation 1c.

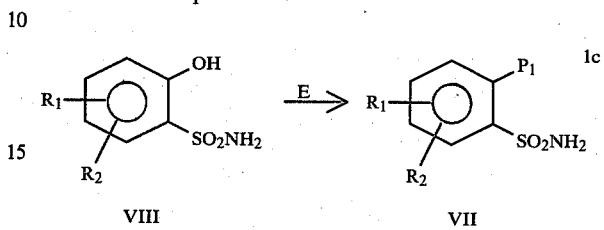

These reactions are best carried out in inert aprotic solvents such as methylene chloride, tetrahydrofuran or acetonitrile at 0°-80° C. One equivalent of the acyl halide or anhydride is used with one equivalent of a tertiary amine such as pyridine, triethylamine or 4-dimethylaminopyridine. Isolation of the product is achieved by evaporation of the solvent and recrystallization from suitable solvents or chromatography on silica gel.

Certain sulfonyl chlorides of Formula X can best be prepared by chlorosulfonation of a substituted phenol, according to the teaching of H. T. Clarke, et al., *Org. Syn. Coll. Vol.* 1, 2nd Ed., 1941, p. 85.

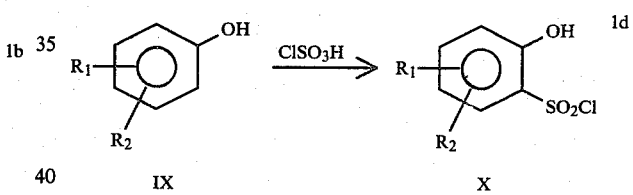

Alternatively, o-hydroxybenzenesulfonamides of Formula XII, and thus some of the sulfonamides of Formula VII, can be prepared by cleavage of an appropriately substituted o-methoxybenzenesulfonamide of Formula XI with sodium thioethoxide in boiling dimethylformamide, according to the teaching of G. I. Feutrill and R. N. Mirrington, *Tetrahedron Letters*, 1327 (1970). This reaction is shown in Equation 1e.

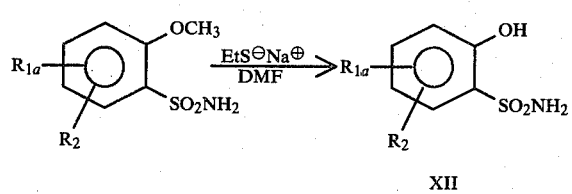

wherein
$R_{1a}$ is H, F, Cl, Br or $C_1$-$C_3$ alkyl; and
$R_2$ is as defined for compound I.

The reaction is best carried out by addition of the o-methoxybenzenesulfonamide XI in dry dimethylformamide (DMF) to a solution of sodium thioethoxide in DMF, prepared by the action of a strong base such as sodium hydride on ethanethiol in DMF. The reaction mixture is boiled under reflux (140° C.) for 3 hours, cooled and the solvent is decanted and/or stripped from the sodium salt of the product XIX. Suspension in water, acidification, extraction with an appropriate solvent such as ethyl acetate, chloroform or diethyl ether and removal of the solvent in vacuo leaves compounds of Formula XII.

o-Methoxybenzenesulfonamides of Formula XI can best be prepared by reaction of the corresponding o-methoxybenzenesulfonyl chlorides with anhydrous ammonia in diethyl ether or tetrahydrofuran or ammonium hydroxide solution. Certain o-methoxybenzenesulfonyl chlorides can be prepared by the method shown in Equation 1f. Diazotization of the appropriate o-methoxyaniline with sodium nitrate in dilute sulfuric acid is followed by reaction of the diazonium salt with sulfur dioxide and cupric chloride in acetic acid and hydrochloric acid at 40° C. with n-butyl chloride as a co-solvent, according to the teaching of *Ukr. Khim. Zh.* 35(8) 821-3 (1969) [CA72 43066e(70)].

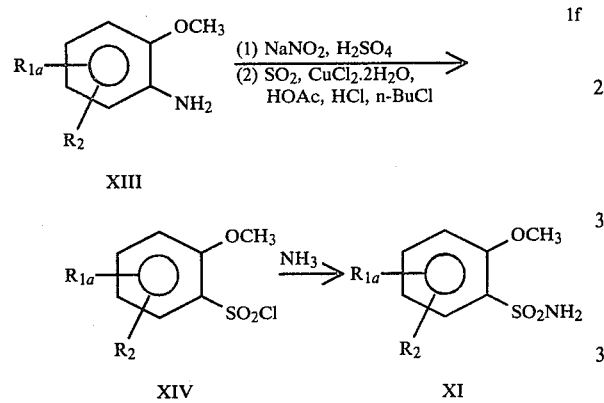

1f

Alternatively, m-methoxybenzenesulfonyl chlorides XVI can be prepared as shown in Equation 1g, according to the teachings of J. E. Cooper and J. M. Paul, *J. Org. Chem.* 35, 2046 (1970) and H. Graafland, et al., *J. Am. Chem. Soc.* 101, 6981 (1979), from 2-hydroxyanisole derivatives XV.

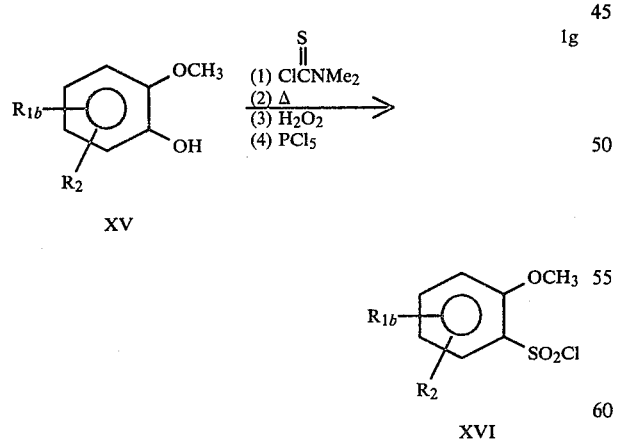

1g wherein
R$_{1b}$ is H, F, Cl, Br, C$_1$-C$_3$ alkyl, NO$_2$, C$_1$-C$_3$ alkoxy or CF$_3$; and
R$_2$ is as defined in Formula I.

The choice of any of the above methods outlined for the preparation of compounds of Formula VII would depend upon the nature of the aromatic substituents, and would be obvious to one skilled in the art.

Many of the compounds of Formula I can be prepared as shown in Equation 2a by reaction of an appropriately substituted o-hydroxybenzenesulfonylurea II with an appropriate acylating reagent G [an acyl halide or anhydride, or an isocyanate, i.e.,

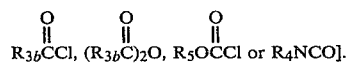

Method 2

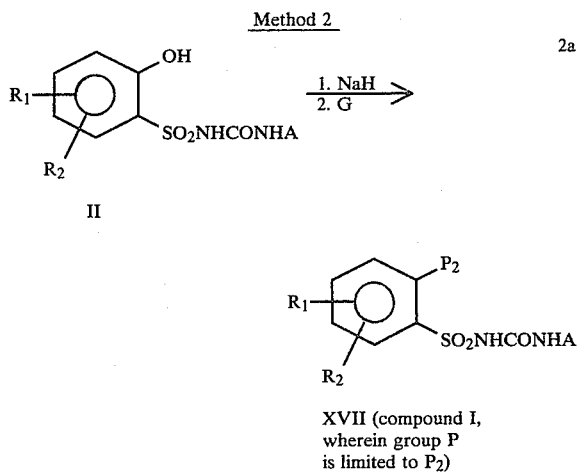

2a

XVII (compound I, wherein group P is limited to P$_2$)

wherein
G is an acylating reagent for addition of the group

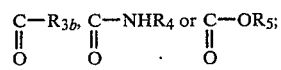

P$_2$ is

R$_{3b}$ is C$_1$-C$_5$ alkyl; C$_2$-C$_3$ alkenyl; C$_2$-C$_3$ alkynyl; C$_1$-C$_4$ alkyl substituted with 1-3 substituents selected from 0-3 F, 0-3 Cl, 0-3 Br and OCH$_3$; C$_2$-C$_3$ alkenyl substituted with Cl; C$_3$-C$_6$ cycloalkyl; or

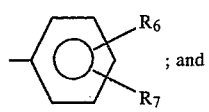

; and

A, R$_1$, R$_2$, R$_4$, R$_5$, R$_6$, R$_7$, R$_8$ and R$_9$ are as defined in Formula I.

The reaction of Equation 2a can be carried out in inert solvents such as tetrahydrofuran (THF) or dioxane at about −10° to 80°. At least one equivalent of sodium hydride is added to compound II dissolved or suspended in the solvent. When the evolution of hydrogen is substantially complete, one equivalent of reagent G is added to the reaction mixture which is then allowed to come to room temperature. Isolation of the product XVII can be accomplished by evaporation of the solvent and optional further purification by recrystallization from suitable solvents or by column chromatography on silica gel.

Many of the o-hydroxybenzenesulfonylureas of Formula II can be prepared by the method outlined in Equation 2b.

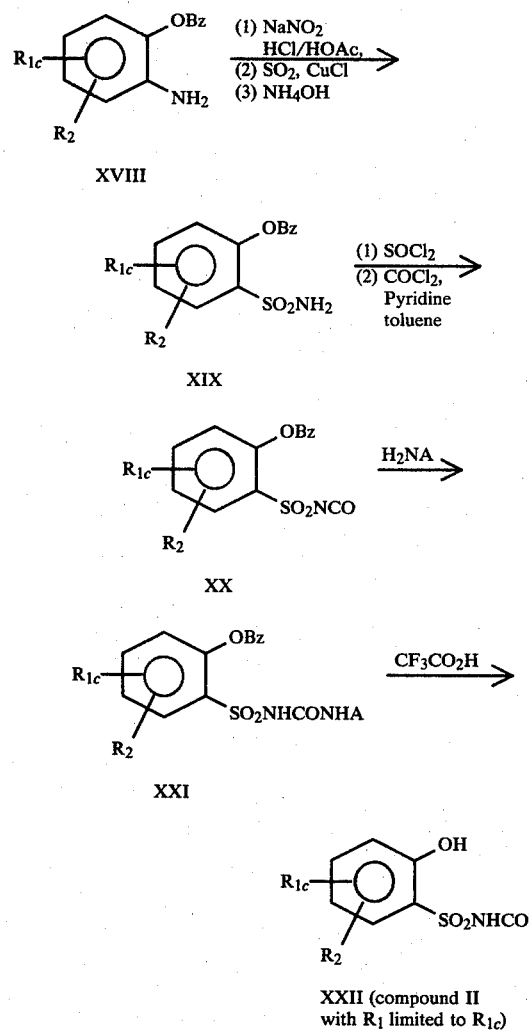

wherein
Bz is benzyl;
$R_{1c}$ is H, F, Cl, Br, $C_1$-$C_3$ alkyl, $NO_2$, $C_1$-$C_3$ alkoxy or $CF_3$; and
$R_2$ and A are as defined in Formula I.

The 2-(benzyloxy)anilines XIX [Chem. Berichte 58, 79 (1925)] can be diazotized in the usual manner and converted to the sulfonyl chloride by coupling with sulfur dioxide and cuprous chloride. Reaction of the sulfonyl chloride with concentrated ammonium hydroxide solution affords the 2-(benzyloxy)benzenesulfonamides XIX. The corresponding sulfonyl isocyanates XX can be prepared by the method of Ulrich, et al., J. Org. Chem. 34, 3200 (1969). The sulfonamide is boiled under reflux with an excess of thionyl chloride which functions as a reactant and solvent. An overnight reaction period is generally sufficient. The thionyl chloride is evaporated and the residue dissolved in an inert solvent such as toluene or xylene, contacted with a catalytic amount of pyridine, then with at least one equivalent of phosgene. The mixture is heated to about 60°–140°, with 80°–100° preferred. The mixture containing the sulfonyl isocyanate can be used directly for the next reaction step or the sulfonyl isocyanate can be isolated by filtration and evaporation of the solvent. The isocyanate can be redissolved in a suitable solvent such as methylene chloride, toluene or acetonitrile and the solution contacted with the amino heterocycle, $ANH_2$ to provide the 2-(benzyloxy)sulfonylurea XXI. Conveniently, the starting reaction temperature is ambient but can be varied from about 0° to 100° if desired. The product can be isolated by filtration if it precipitates from the reaction mixture, otherwise, the solvent can be evaporated and the residual product obtained thereby, with optional further purification obtained by trituration with an organic solvent in which the product is sparingly soluble, such as diethyl ether or 1-chlorobutane and filtration.

The benzyl protecting group can be removed by treatment of the 2-(benzyloxy)benzenesulfonylurea with trifluoroacetic acid according to the teaching of J. P. Marsh and L. Goodman, J. Org. Chem. 30, 2491 (1965). The benzyl ether is dissolved in trifluoroacetic acid and heated from 50°–80° C. for 0.5-3 hours. The reaction progess can be monitored by proton magnetic resonance spectrum and halted upon complete cleavage of the benzyl ether. The trifluoroacetic acid is evaporated in vacuo and the residue can be stirred with solvents such as 1-chlorobutane or ethyl ether to help purify the product XXII. Optional further purification may be performed by dissolving the product in a solvent such as acetone and reprecipitation with a nonpolar solvent such as hexane, or by column chromatography on silica gel.

The synthesis of heterocyclic amines has been reviewed in "The Chemistry of Heterocyclic Compounds" a series published by Interscience Publ., New York and London. 2-Aminopyrimidines are described by D. J. Brown in The Pyrimidines, Vol. XVI of this series. The 2-amino-1,3,5-triazines are reviewed by K. R. Huffman and in the Triazines of this same series. The synthesis of triazines are also described by F. C. Schaefer, U.S. Pat. No. 3,154,547 and by K. R. Huffman and F. C. Schaeffer, J. Org. Chem. 28, 1816–1821 (1963).

The preparation of the aminoheterocycles described by the following formula varies according to the definition of $Y_1$ and Q.

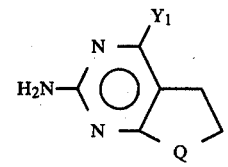

Braker, Sheehan, Spitzmiller and Lott, J. Am. Chem. Soc. 69, 3072 (1947) describe the preparation of 6,7-dihydro-4-methoxy-5H-cyclopentapyrimidin-2-amine by the following sequence of reactions.

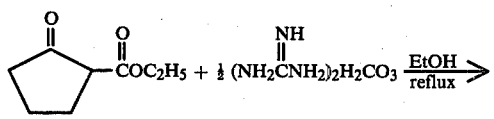

-continued

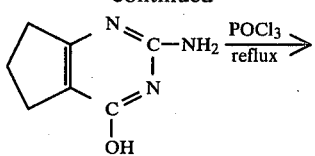

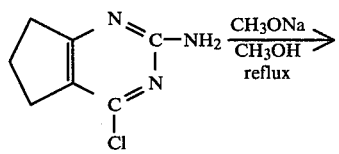

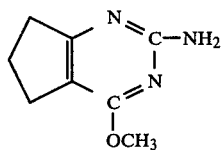

6,7-dihydro-4-methoxy-5H—cyclopentapyrimidin-2-amine.

Similarly, 6,7-dihydro-4-methyl-5H-cyclopentapyrimidin-2-amine can be prepared by the condensation of 2-acetylcyclopentanone with guanidine carbonate, but preferably under acidic conditions, removing the water formed.

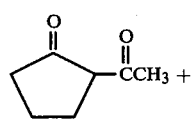

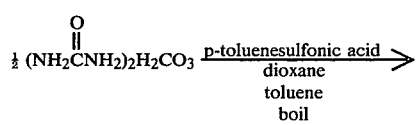

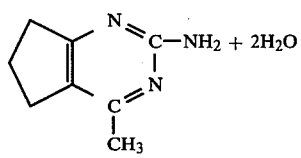

6,7-dihydro-4-methyl-5H—cyclopentapyrimidin-2-amine.

Shrage and Hitchings, J. Org. Chem. 16, 1153 (1951) describe the preparation of 5,6-dihydro-4-methylfuro[2,3-d]pyrimidin-2-amine by the following sequence of reactions.

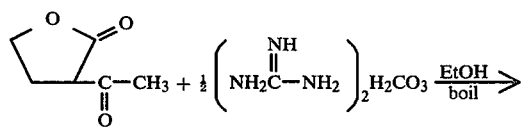

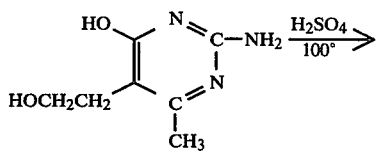

-continued

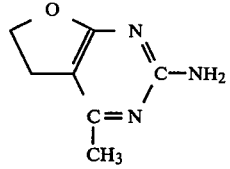

5,6-Dihydro-4-methoxyfuro[2,3-d]pyrimidin-2-amine can be prepared by the method of Braker et al., J. Am. Chem. Soc. 69, 3072 (1947), using 5,6-dihydro-4-hydroxyfuro[2,3-d]pyrimidin-2-amine [Svab, Budesinski and Vavrina, Collection Czech. Chem. Commun. 32, 1582 (1967)].

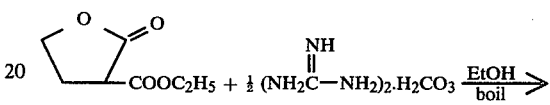

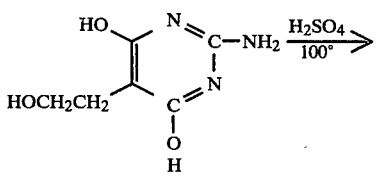

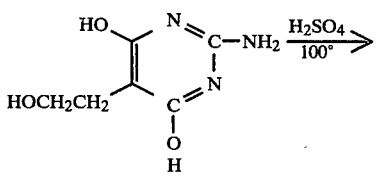

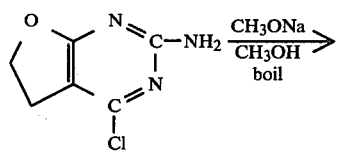

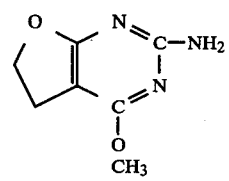

Caldwell, Kornfeld and Donnell, J. Am. Chem. Soc. 63, 2188 (1941), describe the preparation of 6,7-dihydro-5H-cyclopentapyrimidin-2-amine by the following sequence of reactions.

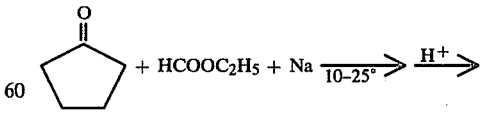

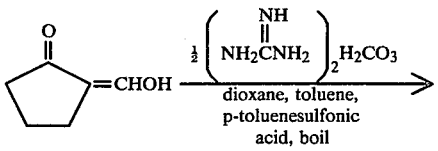

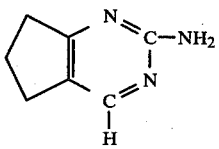

Fissekis, Myles and Brown, J. Org. Chem. 29, 2670 (1964), describe the preparation of 2-amino-4-hydroxy-5-(2-hydroxyethyl)pyrimidine which can be converted to 5,6-dihydrofuro[2,3-d]pyrimidin-2-amine by dehydration.

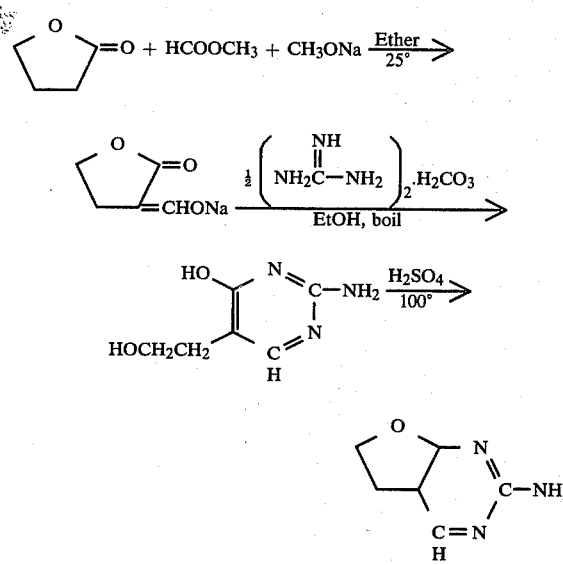

Agriculturally suitable salts of compounds of Formula I are also useful herbicides and can be prepared by a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The following examples illustrated preparation of compounds of this invention, wherein temperatures are in degrees centigrade.

EXAMPLE 1 a. 3,5-Dichloro-2-hydroxybenzenesulfonamide

A solution of 26.1 gm (0.1 mole) 3,5-dichloro-2-hydroxybenzenesulfonyl chloride in 400 ml dry tetrahydrofuran was cooled to 0° with an ice bath, and 11 ml (0.5 mole) anhydrous ammonia was added dropwise, with stirring. The rate of addition was sufficiently slow so as to keep the temperature of the reaction medium less than 10°. The mixture was stirred for 1.5 hours at 0° then slowly warmed to room temperature. The solvent was removed in vacuo and the residue was treated with 100 ml $H_2O$. A small amount of insoluble by-product was filtered off and then the aqueous solution was acidified to pH=2.0 with 1 N HCl solution. Filtration of the resulting white precipitate and drying of the precipitate at 50° under vacuum gave 23.6 gm (97%) white solid, m.p. >225°. The infrared spectrum showed strong absorption at 3300, 1540, 1450 and 1320 cm$^{-1}$, and the nuclear magnetic resonance spectrum showed a broad singlet at 7.2δ, 3 protons, and a doublet of doublets at 7.8δ, 2 protons. These data are consistent with the desired product.

b. 2-Acetoxy-3,5-dichlorobenzenesulfonamide 3,5-Dichloro-2-hydroxybenzenesulfonamide (10.8 gm, 0.045 mole) was dissolved in 100 ml tetrahydrofuran containing 3.6 gm (0.045 mole) pyridine. The mixture was cooled to −10° by an ice bath and then 4.6 ml (0.045 mole) acetic anhydride dissolved in 10 ml tetrahydrofuran was added dropwise, with stirring, over 30 minutes. The mixture was then warmed to ambient temperature and stirred for 4 to 5 hours. The solvent was removed in vacuo and treated with 500 ml water. The aqueous solution was extracted three times with 250 ml of diethyl ether. The combined organic extracts were washed 3 times with 100 ml each 1 N hydrochloric acid and once with 200 ml brine. After drying over $Na_2SO_4$, the ether was removed in vacuo to yield 10.8 gm (84.5%) of a white solid, m.p. 139°–143°. The infrared spectrum showed strong absorbances at 3400 ($NH_2$),

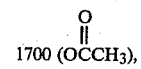

1620, 1570, 1360, 1120–1200 cm$^{-1}$ and the nuclear magnetic resonance spectrum (in acetone-d$_6$) showed a singlet at 2.33δ, 3H; broad singlet at 5.2δ,2H; and a singlet at 7.7δ, 2H, corresponding to the methyl, sulfonamide and aromatic protons, respectively, of the desired product.

c. N-[(4-Methoxy-6-methylpyrimidin-2-yl)aminocarbonyl]-2-acetoxy-3,5-dichlorobenzenesulfonamide A mixture of 6.0 gm (0.02 mole) 2-acetoxy-3,5-dichlorobenzenesulfonamide, 0.1 gm 1,4-diaza[2.2.2-]bicyclooctane (DABCO), 2.8 ml (0.025 mole) n-butyl isocyanate and 50 ml dry xylenes was heated to reflux and maintained at that temperature for 1 hour. Phosgene (0.03 mole, 1.3 ml) was then added dropwise, so as to maintain the reaction temperature >130°. The reaction mixture was boiled under reflux for 3 hours after addition of phosgene, then cooled and filtered. The solvent was removed in vacuo and the residue was dissolved in 20 ml of methylene chloride and added directly to a stirred solution of 2-amino-4-methoxy-6-methylpyrimidine in 10 ml methylene chloride. The reaction was protected from atmospheric moisture and stirred overnight. Filtration of the solution removed excess starting material and the solution was evaporated to a residue. The residue was washed with 1-butyl chloride and filtered, giving 1.4 g (0.003 mole, 22% yield) of the sulfonylurea product. The nuclear magnetic resonance of the product shows peaks as follows: (singlet, 2.0δ, 3H, singlet, 2.2δ, 3H; singlet, 3.9δ, 3H; singlet, 6.1δ, 1H; 7.5–8.2δ, multiplet, 2H; br singlet, 8.6δ, 1H), consistent with the desired product.

EXAMPLE 2

N-[(4,6-Dimethylpyrimidin-2-yl)aminocarbonyl]-2-hydroxybenzenesulfonamide a. 2-(Benzyloxy)benzenesulfonamide To 148 ml of concentrated hydrochloric acid and 45 ml of acetic acid, maintained at <10°, was added 39.2 g of 2-(benzyloxy)aniline [See Berichte, 58, 79 (1925)]. White solid formed. Sufficient additional acetic acid was added to render the mixture stirrable. While temperature was 0° to 3°, a solution of 28 g of sodium nitrite in 75 ml of water was dripped into it. The mixture was kept at 5° to 10° for 15 minutes, then added to a mixture of 5.2 g of cuprous chloride, 37 ml of sulfur dioxide and 211 ml of acetic acid at 3°. Next, 290 ml of butyl chloride was added and the mixture allowed to warm to ambient temperature. After 16 hours, the mixture was diluted with water and the organic layer washed with water and dilute sodium bicarbonate solution until the washings were basic. The mixture was then dried (MgSO$_4$) and evaporated to an oil (A). The effervescing aqueous portion (from which the butyl chloride solution had been removed) was depositing an oil; it was then treated portionwise with sodium bisulfite over several hours. After about 16 hours the oil was extracted into butyl chloride and the butyl chloride solution washed, dried and evaporated, providing an oil (B). Oils A and B are 2-(benzyloxy)benzenesulfonyl chloride. To oils A and B was added an excess of concentrated aqueous ammonia, the mixture was swirled and a white solid was observed. The solid was filtered off and extracted with hot butyl chloride; upon cooling, the extract precipitated 2-(benzyloxy)benzenesulfonamide as a white solid, m.p. 127°–129°.

b.

N-[(4,6-Dimethylpyrimidin-2-yl)aminocarbonyl]-2-(benzyloxy)benzenesulfonamide

A solution of 5.4 g of the sulfonamide (from a, above) in 40 ml of thionyl chloride was boiled under reflux for 39 hours. The solution was evaporated to an oil and the oil dissolved in 40 ml of a 13.8% phosgene solution in toluene. Three drops of pyridine was added and the mixture heated for 2 hours at 85° under phosgene reflux. The mixture was then filtered and evaporated to an oil, 2-(benzyloxy)benzensulfonyl isocyanate. The infrared spectrum showed a strong absorption peak at 2230 cm$^{-1}$, characteristic of a sulfonyl isocyanate.

Addition of 2.52 g of 2-amino-4,6-dimethylpyrimidine to a solution of the isocyanate in acetonitrile resulted in an exothermic reaction and precipitation of a white solid. After 2 hours, the solid was filtered off and washed with acetonitrile and butyl chloride, leaving N-[(4,6-dimethylpyrimidin-2-yl)aminocarbonyl]-2-(benzyloxy)benzenesulfonamide as a white solid, m.p. 218° (dec.). The infrared spectrum showed an absorption peak at 1700 cm$^{-1}$ for the urea carbonyl group. The mass spectrum showed

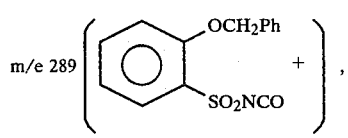

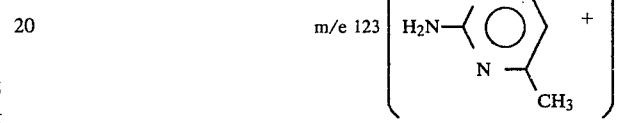

and m/e 91 (PhCH$_2$+).

c.

N-[(4,6-Dimethylpyrimidin-2-yl)aminocarbonyl]-2-hydroxybenzenesulfonamide

A stirred solution of 0.5 g of N-[(4,6-dimethylpyrimidin-2-yl)aminocarbonyl]-2-(benzyloxy)benzenesulfonamide (from b, above) in 20 ml of trifluoroacetic acid was boiled under reflux for 1.5 hours. The proton magnetic resonance spectrum indicated complete cleavage of the benzyl ether. The trifluoroacetic acid was evaporated in vacuum and the oily residue stirred with water and diethyl ether, providing white solid. The solid was dissolved in acetone and reprecipitated by dilution of the solution with hexane, yielding N-[(4,6-dimethylpyrimidin-2-yl)aminocarbonyl]-2-hydroxybenzenesulfonamide as a white solid, m.p. ca. 180°. The mass spectrum showed a molecular ion, m/e 322;

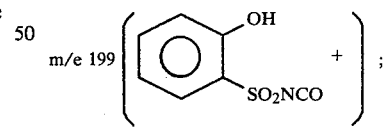

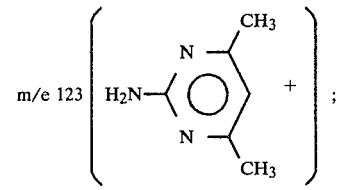

and no m/e 91 (no Ph—CH$_2$+).

By the procedures of Examples 1 and 2 and the methods discussed, the following compounds can be prepared by one skilled in the art.

TABLE I

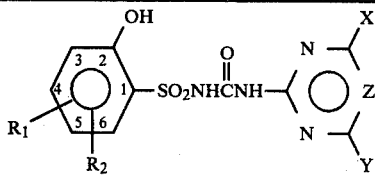

| R₁ | R₂ | X | Y | Z |
|---|---|---|---|---|
| H | H | CH₃ | CH₃ | CH |
| H | H | CH₃O | CH₃ | CH |
| H | H | CH₃O | CH₃O | CH |
| 5-F | H | CH₃ | CH₃ | CH |
| 3-Cl | H | CH₃ | CH₃ | CH |
| 4-Cl | H | CH₃ | CH₃ | CH |
| 5-Cl | 3 | CH₃ | CH₃ | CH |
| 6-Cl | H | CH₃ | CH₃ | CH |
| 5-Br | H | CH₃ | CH₃ | CH |
| 3-CH₃ | H | CH₃ | CH₃ | CH |
| 6-CH₃ | H | CH₃ | CH₃ | CH |
| 6-(CH₃)₂CH | H | CH₃ | CH₃ | CH |
| 5-NO₂ | H | CH₃ | CH₃ | CH |
| 5-CH₃O | H | CH₃ | CH₃ | CH |
| 5-(CH₃)₂CHO | H | CH₃ | CH₃ | CH |
| 5-CF₃ | H | CH₃ | CH₃ | CH |
| 5-OCOCH₃ | H | CH₃ | CH₃ | CH |
| 3-CH₃ | 5-CH₃ | CH₃ | CH₃ | CH |
| 3-Cl | 5-Cl | CH₃ | CH₃ | CH |
| 3-Cl | 5-CH₃ | CH₃ | CH₃ | CH |
| H | H | CH₃ | CH₃ | N |
| H | H | CH₃O | CH₃ | N |
| H | H | CH₃O | CH₃O | N |
| H | H | CH₃ | CH₃ | CCl |
| H | H | CH₃ | CH₃ | CBr |
| H | H | CH₃ | CH₃ | CCN |
| H | H | CH₃ | CH₃ | CCH₃ |
| H | H | CH₃ | CH₃ | CC₂H₅ |
| H | H | CH₃ | CH₃ | CCH₂CH₂Cl |
| H | H | CH₃ | CH₃ | CCH₂CH=CH₂ |
| H | H | H | CH₃ | CH |
| H | H | Cl | OCH₃ | CH |
| H | H | Br | OCH₃ | CH |
| H | H | C₂H₅ | CH₃ | CH |
| H | H | CH₃CH₂CH₂O | OCH₃ | CH |
| H | H | CF₃ | CH₃ | CH |
| H | H | CH₃S | CH₃O | CH |
| H | H | CH₃OCH₂ | CH₃ | CH |
| H | H | H | CH₃ | N |

TABLE I-continued

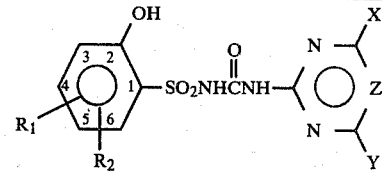

| R₁ | R₂ | X | Y | Z |
|---|---|---|---|---|
| H | H | Cl | OCH₃ | N |
| H | H | Br | OCH₃ | N |
| H | H | C₂H₅ | CH₃ | N |
| H | H | CH₃CH₂CH₂O | OCH₃ | N |
| H | H | CF₃ | CH₃ | N |
| H | H | CH₃S | CH₃O | N |
| H | H | CH₃OCH₂ | CH₃ | N |

TABLE II

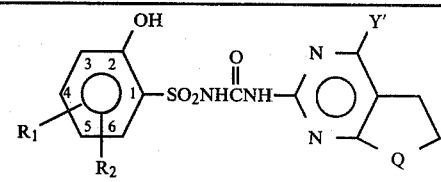

| R₁ | R₂ | Y' | Q |
|---|---|---|---|
| 3-Cl | 5-Cl | H | O |
| 3-Cl | 5-Cl | CH₃ | O |
| 3-Cl | 5-Cl | OCH₃ | O |
| 3-Cl | 5-Cl | Cl | O |
| 3-Cl | 5-Cl | H | CH₂ |
| 3-Cl | 5-Cl | CH₃ | CH₂ |
| 3-Cl | 5-Cl | OCH₃ | CH₂ |
| 3-Cl | 5-Cl | Cl | CH₂ |
| H | H | H | O |
| H | H | CH₃ | O |
| H | H | OCH₃ | O |
| H | H | Cl | O |
| H | H | H | CH₂ |
| H | H | CH₃ | CH₂ |
| H | H | OCH₃ | CH₂ |
| H | H | Cl | CH₂ |

TABLE III

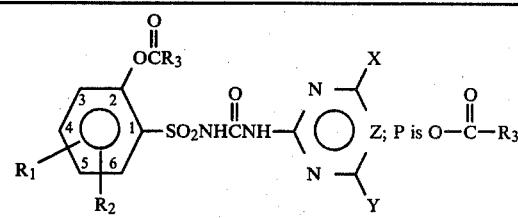

| R₁ | R₂ | R₃ | X | Y | Z | m.p. (°C.) |
|---|---|---|---|---|---|---|
| H | H | H | CH₃ | CH₃ | CH | |
| H | H | CH₃ | CH₃ | CH₃ | CH | |
| H | H | CH₃(CH₂)₄ | CH₃ | CH₃ | CH | |
| H | H | CH₂=CH | CH₃ | CH₃ | CH | |
| H | H | CH₂=CHCH₂ | CH₃ | CH₃ | CH | |
| H | H | HC≡C | CH₃ | CH₃ | CH | |
| H | H | CH₃C≡C | CH₃ | CH₃ | CH | |
| H | H | ClCH₂ | CH₃ | CH₃ | CH | |
| H | H | BrCH₂ | CH₃ | CH₃ | CH | |
| H | H | Cl₃C | CH₃ | CH₃ | CH | |
| H | H | Br₃C | CH₃ | CH₃ | CH | |
| H | H | F₃C | CH₃ | CH₃ | CH | |
| H | H | CH₃OCH₂ | CH₃ | CH₃ | CH | |
| H | H | Cl(CH₂)₄ | CH₃ | CH₃ | CH | |
| H | H | ClCH=CH | CH₃ | CH₃ | CH | |
| H | H | ClCH₂CH=CH | CH₃ | CH₃ | CH | |

TABLE III-continued

Structure:
$$\text{2-(OCR}_3\text{C(=O))-phenyl-SO}_2\text{NHC(=O)NH-[pyrimidine/triazine with X, Y substituents]}; \text{ P is O-C(=O)-R}_3$$

| R₁ | R₂ | R₃ | X | Y | Z | m.p. (°C.) |
|---|---|---|---|---|---|---|
| H | H | cyclopropyl | CH₃ | CH₃ | CH | |
| H | H | cyclopentyl | CH₃ | CH₃ | CH | |
| H | H | cyclohexyl | CH₃ | CH₃ | CH | |
| H | H | phenyl | CH₃ | CH₃ | CH | |
| H | H | 4-O₂N-phenyl | CH₃ | CH₃ | CH | |
| H | H | 4-CH₃-phenyl | CH₃ | CH₃ | CH | |
| H | H | 4-Cl-phenyl | CH₃ | CH₃ | CH | |
| H | H | 4-CH₃O-phenyl | CH₃ | CH₃ | CH | |
| H | H | 3-Cl-phenyl | CH₃ | CH₃ | CH | |
| H | H | 2-Cl-phenyl | CH₃ | CH₃ | CH | |
| H | H | 2,4-Cl₂-phenyl | CH₃ | CH₃ | CH | |
| H | H | H | CH₃O | CH₃ | CH | |
| H | H | CH₃ | CH₃O | CH₃ | CH | |
| H | H | CH₃(CH₂)₄ | CH₃O | CH₃ | CH | |
| H | H | CH₂=CH | CH₃O | CH₃ | CH | |
| H | H | CH₂=CHCH₂ | CH₃O | CH₃ | CH | |
| H | H | HC≡C | CH₃O | CH₃ | CH | |
| H | H | CH₃C≡C | CH₃O | CH₃ | CH | |
| H | H | ClCH₂ | CH₃O | CH₃ | CH | |
| H | H | BrCH₂ | CH₃O | CH₃ | CH | |
| H | H | Cl₃C | CH₃O | CH₃ | CH | |
| H | H | Br₃C | CH₃O | CH₃ | CH | |
| H | H | F₃C | CH₃O | CH₃ | CH | |
| H | H | CH₃OCH₂ | CH₃O | CH₃ | CH | |
| H | H | Cl(CH₂)₄ | CH₃O | CH₃ | CH | |
| H | H | ClCH=CH | CH₃O | CH₃ | CH | |
| H | H | ClCH₂CH=CH | CH₃O | CH₃ | CH | |
| H | H | cyclopropyl | CH₃O | CH₃ | CH | |
| H | H | cyclopentyl | CH₃O | CH₃ | CH | |
| H | H | cyclohexyl | CH₃O | CH₃ | CH | |

TABLE III-continued

| R₁ | R₂ | R₃ | X | Y | Z | m.p. (°C.) |
|---|---|---|---|---|---|---|
| H | H | 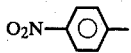 | $CH_3O$ | $CH_3$ | CH | |
| H | H | 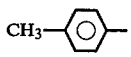 | $CH_3O$ | $CH_3$ | CH | |
| H | H | 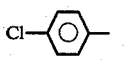 | $CH_3O$ | $CH_3$ | CH | |
| H | H | 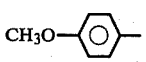 | $CH_3O$ | $CH_3$ | CH | |
| H | H | 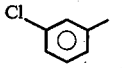 | $CH_3O$ | $CH_3$ | CH | |
| H | H | 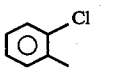 | $CH_3O$ | $CH_3$ | CH | |
| H | H | 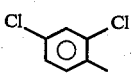 | $CH_3O$ | $CH_3$ | CH | |
| H | H |  | $CH_3O$ | $CH_3$ | CH | |
| H | H | H | $CH_3O$ | $CH_3O$ | CH | |
| H | H | $CH_3$ | $CH_3O$ | $CH_3O$ | CH | |
| H | H | $CH_3(CH_2)_4$ | $CH_3O$ | $CH_3O$ | CH | |
| H | H | $CH_2=CH$ | $CH_3O$ | $CH_3O$ | CH | |
| H | H | $CH_2=CHCH_2$ | $CH_3O$ | $CH_3O$ | CH | |
| H | H | $HC\equiv C$ | $CH_3O$ | $CH_3O$ | CH | |
| H | H | $CH_3C\equiv C$ | $CH_3O$ | $CH_3O$ | CH | |
| H | H | $ClCH_2$ | $CH_3O$ | $CH_3O$ | CH | |
| H | H | $BrCH_2$ | $CH_3O$ | $CH_3O$ | CH | |
| H | H | $Cl_3C$ | $CH_3O$ | $CH_3O$ | CH | |
| H | H | $Br_3C$ | $CH_3O$ | $CH_3O$ | CH | |
| H | H | $F_3C$ | $CH_3O$ | $CH_3O$ | CH | |
| H | H | $CH_3OCH_2$ | $CH_3O$ | $CH_3O$ | CH | |
| H | H | $Cl(CH_2)_4$ | $CH_3O$ | $CH_3O$ | CH | |
| H | H | $ClCH=CH$ | $CH_3O$ | $CH_3O$ | CH | |
| H | H | $ClCH_2CH=CH$ | $CH_3O$ | $CH_3O$ | CH | |
| H | H |  | $CH_3O$ | $CH_3O$ | CH | |
| H | H |  | $CH_3O$ | $CH_3O$ | CH | |
| H | H |  | $CH_3O$ | $CH_3O$ | CH | |
| H | H | 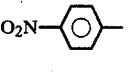 | $CH_3O$ | $CH_3O$ | CH | |
| H | H |  | $CH_3O$ | $CH_3O$ | CH | |

TABLE III-continued

Structure: benzene ring with OC(O)R₃ at position 2, SO₂NHCNH-C(=O)- at position 1, connected to pyrimidine/triazine ring with X and Y substituents; R₁ at position 5, R₂ at position 6; Z; P is O—C(=O)—R₃

| R₁ | R₂ | R₃ | X | Y | Z | m.p. (°C.) |
|---|---|---|---|---|---|---|
| H | H | CH₃-C₆H₄- (p-tolyl) | CH₃O | CH₃O | CH | |
| H | H | Cl-C₆H₄- (p-chlorophenyl) | CH₃O | CH₃O | CH | |
| H | H | CH₃O-C₆H₄- (p-methoxyphenyl) | CH₃O | CH₃O | CH | |
| H | H | Cl-C₆H₄- (m-chlorophenyl) | CH₃O | CH₃O | CH | |
| H | H | o-Cl-C₆H₄- | CH₃O | CH₃O | CH | |
| H | H | 2,4-Cl₂-C₆H₃- | CH₃O | CH₃O | CH | |
| H | H | H | CH₃ | CH₃ | N | |
| H | H | CH₃ | CH₃ | CH₃ | N | |
| H | H | CH₃(CH₂)₄ | CH₃ | CH₃ | N | |
| H | H | CH₂=CH | CH₃ | CH₃ | N | |
| H | H | CH₂=CHCH₂ | CH₃ | CH₃ | N | |
| H | H | HC≡C | CH₃ | CH₃ | N | |
| H | H | CH₃C≡C | CH₃ | CH₃ | N | |
| H | H | ClCH₂ | CH₃ | CH₃ | N | |
| H | H | BrCH₂ | CH₃ | CH₃ | N | |
| H | H | Cl₃C | CH₃ | CH₃ | N | |
| H | H | Br₃C | CH₃ | CH₃ | N | |
| H | H | F₃C | CH₃ | CH₃ | N | |
| H | H | CH₃OCH₂ | CH₃ | CH₃ | N | |
| H | H | Cl(CH₂)₄ | CH₃ | CH₃ | N | |
| H | H | ClCH=CH | CH₃ | CH₃ | N | |
| H | H | ClCH₂CH=CH | CH₃ | CH₃ | N | |
| H | H | cyclopropyl | CH₃ | CH₃ | N | |
| H | H | cyclopentyl | CH₃ | CH₃ | N | |
| H | H | cyclohexyl | CH₃ | CH₃ | N | |
| H | H | phenyl | CH₃ | CH₃ | N | |
| H | H | O₂N-C₆H₄- | CH₃ | CH₃ | N | |
| H | H | CH₃-C₆H₄- | CH₃ | CH₃ | N | |
| H | H | Cl-C₆H₄- | CH₃ | CH₃ | N | |

TABLE III-continued

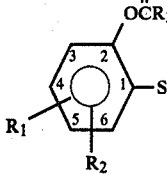
Z; P is O—C(=O)—R₃

| R₁ | R₂ | R₃ | X | Y | Z | m.p. (°C.) |
|---|---|---|---|---|---|---|
| H | H |  (CH₃O—Ph—) | CH₃ | CH₃ | N | |
| H | H |  (Cl—Ph—, meta) | CH₃ | CH₃ | N | |
| H | H |  (ortho-Cl-Ph-) | CH₃ | CH₃ | N | |
| H | H |  (2,4-di-Cl-Ph-) | CH₃ | CH₃ | N | |
| H | H | H | CH₃O | CH₃ | N | |
| H | H | CH₃ | CH₃O | CH₃ | N | |
| H | H | CH₃(CH₂)₄ | CH₃O | CH₃ | N | |
| H | H | CH₂=CH | CH₃O | CH₃ | N | |
| H | H | CH₂=CHCH₂ | CH₃O | CH₃ | N | |
| H | H | HC≡C | CH₃O | CH₃ | N | |
| H | H | CH₃C≡C | CH₃O | CH₃ | N | |
| H | H | ClCH₂ | CH₃O | CH₃ | N | |
| H | H | BrCH₂ | CH₃O | CH₃ | N | |
| H | H | Cl₃C | CH₃O | CH₃ | N | |
| H | H | Br₃C | CH₃O | CH₃ | N | |
| H | H | F₃C | CH₃O | CH₃ | N | |
| H | H | CH₃OCH₂ | CH₃O | CH₃ | N | |
| H | H | Cl(CH₂)₄ | CH₃O | CH₃ | N | |
| H | H | ClCH=CH | CH₃O | CH₃ | N | |
| H | H | ClCH₂CH=CH | CH₃O | CH₃ | N | |
| H | H |  (cyclopropyl) | CH₃O | CH₃ | N | |
| H | H |  (cyclopentyl) | CH₃O | CH₃ | N | |
| H | H |  (cyclohexyl) | CH₃O | CH₃ | N | |
| H | H | 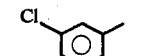 (phenyl) | CH₃O | CH₃ | N | |
| H | H | 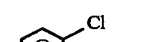 (O₂N—Ph—) | CH₃O | CH₃ | N | |
| H | H | 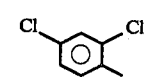 (CH₃—Ph—) | CH₃O | CH₃ | N | |
| H | H |  (Cl—Ph—) | CH₃O | CH₃ | N | |
| H | H |  (CH₃O—Ph—) | CH₃O | CH₃ | N | |
| H | H | 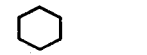 (Cl—Ph—, meta) | CH₃O | CH₃ | N | |

TABLE III-continued

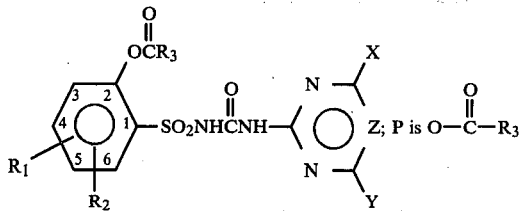

| R₁ | R₂ | R₃ | X | Y | Z | m.p. (°C.) |
|---|---|---|---|---|---|---|
| H | H |  | CH₃O | CH₃ | N | |
| H | H |  | CH₃O | CH₃ | N | |
| H | H | H | CH₃O | CH₃O | N | |
| H | H | CH₃ | CH₃O | CH₃O | N | |
| H | H | CH₃(CH₂)₄ | CH₃O | CH₃O | N | |
| H | H | CH₂=CH | CH₃O | CH₃O | N | |
| H | H | CH₂=CHCH₂ | CH₃O | CH₃O | N | |
| H | H | HC≡C | CH₃O | CH₃O | N | |
| H | H | CH₃C≡C | CH₃O | CH₃O | N | |
| H | H | ClCH₂ | CH₃O | CH₃O | N | |
| H | H | BrCH₂ | CH₃O | CH₃O | N | |
| H | H | Cl₃C | CH₃O | CH₃O | N | |
| H | H | Br₃C | CH₃O | CH₃O | N | |
| H | H | F₃C | CH₃O | CH₃O | N | |
| H | H | CH₃OCH₂ | CH₃O | CH₃O | N | |
| H | H | Cl(CH₂)₄ | CH₃O | CH₃O | N | |
| H | H | ClCH=CH | CH₃O | CH₃O | N | |
| H | H | ClCH₂CH=CH | CH₃O | CH₃O | N | |
| H | H |  | CH₃O | CH₃O | N | |
| H | H |  | CH₃O | CH₃O | N | |
| H | H |  | CH₃O | CH₃O | N | |
| H | H |  | CH₃O | CH₃O | N | |
| H | H | 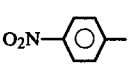 | CH₃O | CH₃O | N | |
| H | H | 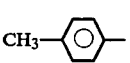 | CH₃O | CH₃O | N | |
| H | H | 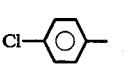 | CH₃O | CH₃O | N | |
| H | H | 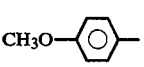 | CH₃O | CH₃O | N | |
| H | H | 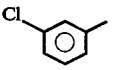 | CH₃O | CH₃O | N | |
| H | H |  | CH₃O | CH₃O | N | |
| H | H |  | CH₃O | CH₃O | N | |
| 3-Cl | 5-Cl | H | CH₃ | CH₃ | CH | 173–175° |
| 3-Cl | 5-Cl | CH₃ | CH₃ | CH₃ | CH | |

TABLE III-continued

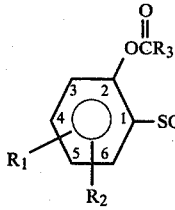

| R₁ | R₂ | R₃ | X | Y | Z | m.p. (°C.) |
|---|---|---|---|---|---|---|
| 3-Cl | 5-Cl | CH₃(CH₂)₄ | CH₃ | CH₃ | CH | |
| 3-Cl | 5-Cl | CH₂=CH | CH₃ | CH₃ | CH | |
| 3-Cl | 5-Cl | CH₂=CHCH₂ | CH₃ | CH₃ | CH | |
| 3-Cl | 5-Cl | HC≡C | CH₃ | CH₃ | CH | |
| 3-Cl | 5-Cl | CH₃C≡C | CH₃ | CH₃ | CH | |
| 3-Cl | 5-Cl | ClCH₂ | CH₃ | CH₃ | CH | |
| 3-Cl | 5-Cl | BrCH₂ | CH₃ | CH₃ | CH | |
| 3-Cl | 5-Cl | Cl₃C | CH₃ | CH₃ | CH | |
| 3-Cl | 5-Cl | Br₃C | CH₃ | CH₃ | CH | |
| 3-Cl | 5-Cl | F₃C | CH₃ | CH₃ | CH | |
| 3-Cl | 5-Cl | CH₃OCH₂ | CH₃ | CH₃ | CH | |
| 3-Cl | 5-Cl | Cl(CH₂)₄ | CH₃ | CH₃ | CH | |
| 3-Cl | 5-Cl | ClCH=CH | CH₃ | CH₃ | CH | |
| 3-Cl | 5-Cl | ClCH₂CH=CH | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl |  | CH₃ | CH₃ | CH | |
| 3-Cl | 5-Cl | 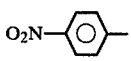 | CH₃ | CH₃ | CH | |
| 3-Cl | 5-Cl | H | CH₃O | CH₃ | CH | 138–143° |
| 3-Cl | 5-Cl | CH₃ | CH₃O | CH₃ | CH | |
| 3-Cl | 5-Cl | CH₃(CH₂)₄ | CH₃O | CH₃ | CH | |
| 3-Cl | 5-Cl | CH₂=CH | CH₃O | CH₃ | CH | |
| 3-Cl | 5-Cl | CH₂=CHCH₂ | CH₃O | CH₃ | CH | |
| 3-Cl | 5-Cl | HC≡C | CH₃O | CH₃ | CH | |
| 3-Cl | 5-Cl | CH₃C≡C | CH₃O | CH₃ | CH | |
| 3-Cl | 5-Cl | ClCH₂ | CH₃O | CH₃ | CH | |
| 3-Cl | 5-Cl | BrCH₂ | CH₃O | CH₃ | CH | |
| 3-Cl | 5-Cl | Cl₃C | CH₃O | CH₃ | CH | |
| 3-Cl | 5-Cl | Br₃C | CH₃O | CH₃ | CH | |
| 3-Cl | 5-Cl | F₃C | CH₃O | CH₃ | CH | |

TABLE III-continued

Structure:
$$\text{Ar}(R_1, R_2, \text{OCR}_3\text{ at position 2})-SO_2NHCNH-\text{pyrimidine}(X, Y, Z); \text{P is } O-C(=O)-R_3$$

| $R_1$ | $R_2$ | $R_3$ | X | Y | Z | m.p. (°C.) |
|---|---|---|---|---|---|---|
| 3-Cl | 5-Cl | CH$_3$OCH$_2$ | CH$_3$O | CH$_3$ | CH | |
| 3-Cl | 5-Cl | Cl(CH$_2$)$_4$ | CH$_3$O | CH$_3$ | CH | |
| 3-Cl | 5-Cl | ClCH=CH | CH$_3$O | CH$_3$ | CH | |
| 3-Cl | 5-Cl | ClCH$_2$CH=CH | CH$_3$O | CH$_3$ | CH | |
| 3-Cl | 5-Cl | cyclopropyl | CH$_3$O | CH$_3$ | CH | |
| 3-Cl | 5-Cl | cyclopentyl | CH$_3$O | CH$_3$ | CH | |
| 3-Cl | 5-Cl | cyclohexyl | CH$_3$O | CH$_3$ | CH | |
| 3-Cl | 5-Cl | phenyl | CH$_3$O | CH$_3$ | CH | |
| 3-Cl | 5-Cl | 4-O$_2$N-C$_6$H$_4$ | CH$_3$O | CH$_3$ | CH | |
| 3-Cl | 5-Cl | 4-CH$_3$-C$_6$H$_4$ | CH$_3$O | CH$_3$ | CH | |
| 3-Cl | 5-Cl | 4-Cl-C$_6$H$_4$ | CH$_3$O | CH$_3$ | CH | |
| 3-Cl | 5-Cl | 4-CH$_3$O-C$_6$H$_4$ | CH$_3$O | CH$_3$ | CH | |
| 3-Cl | 5-Cl | 3-Cl-C$_6$H$_4$ | CH$_3$O | CH$_3$ | CH | |
| 3-Cl | 5-Cl | 2-Cl-C$_6$H$_4$ | CH$_3$O | CH$_3$ | CH | |
| 3-Cl | 5-Cl | 2,4-Cl$_2$-C$_6$H$_3$ | CH$_3$O | CH$_3$ | CH | |
| 3-Cl | 5-Cl | H | CH$_3$O | CH$_3$O | CH | 186–189° |
| 3-Cl | 5-Cl | CH$_3$ | CH$_3$O | CH$_3$O | CH | |
| 3-Cl | 5-Cl | CH$_3$(CH$_2$)$_4$ | CH$_3$O | CH$_3$O | CH | |
| 3-Cl | 5-Cl | CH$_2$=CH | CH$_3$O | CH$_3$O | CH | |
| 3-Cl | 5-Cl | CH$_2$=CHCH$_2$ | CH$_3$O | CH$_3$O | CH | |
| 3-Cl | 5-Cl | HC≡C | CH$_3$O | CH$_3$O | CH | |
| 3-Cl | 5-Cl | CH$_3$C≡C | CH$_3$O | CH$_3$O | CH | |
| 3-Cl | 5-Cl | ClCH$_2$ | CH$_3$O | CH$_3$O | CH | |
| 3-Cl | 5-Cl | BrCH$_2$ | CH$_3$O | CH$_3$O | CH | |
| 3-Cl | 5-Cl | Cl$_3$C | CH$_3$O | CH$_3$O | CH | |
| 3-Cl | 5-Cl | Br$_3$C | CH$_3$O | CH$_3$O | CH | |
| 3-Cl | 5-Cl | F$_3$C | CH$_3$O | CH$_3$O | CH | |
| 3-Cl | 5-Cl | CH$_3$OCH$_2$ | CH$_3$O | CH$_3$O | CH | |
| 3-Cl | 5-Cl | Cl(CH$_2$)$_4$ | CH$_3$O | CH$_3$O | CH | |
| 3-Cl | 5-Cl | ClCH=CH | CH$_3$O | CH$_3$O | CH | |
| 3-Cl | 5-Cl | ClCH$_2$CH=CH | CH$_3$O | CH$_3$O | CH | |
| 3-Cl | 5-Cl | cyclopropyl | CH$_3$O | CH$_3$O | CH | |
| 3-Cl | 5-Cl | cyclopentyl | CH$_3$O | CH$_3$O | CH | |

TABLE III-continued

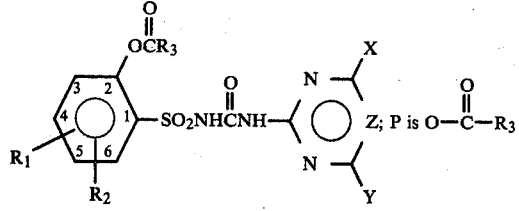

| R₁ | R₂ | R₃ | X | Y | Z | m.p. (°C.) |
|---|---|---|---|---|---|---|
| 3-Cl | 5-Cl |  (cyclohexyl) | CH₃O | CH₃O | CH | |
| 3-Cl | 5-Cl |  (phenyl) | CH₃O | CH₃O | CH | |
| 3-Cl | 5-Cl | O₂N—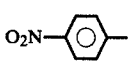— | CH₃O | CH₃O | CH | |
| 3-Cl | 5-Cl | CH₃—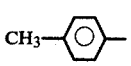— | CH₃O | CH₃O | CH | |
| 3-Cl | 5-Cl | Cl—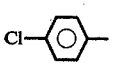— | CH₃O | CH₃O | CH | |
| 3-Cl | 5-Cl | CH₃O—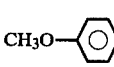— | CH₃O | CH₃O | CH | |
| 3-Cl | 5-Cl | 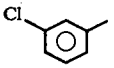 (3-Cl-phenyl) | CH₃O | CH₃O | CH | |
| 3-Cl | 5-Cl | 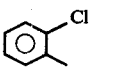 (2-Cl-tolyl) | CH₃O | CH₃ | CH | |
| 3-Cl | 5-Cl | 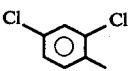 (dichloro-tolyl) | CH₃O | CH₃O | CH | |
| 3-Cl | 5-Cl | H | CH₃ | CH₃ | N | |
| 3-Cl | 5-Cl | CH₃ | CH₃ | CH₃ | N | |
| 3-Cl | 5-Cl | CH₃(CH₂)₄ | CH₃ | CH₃ | N | |
| 3-Cl | 5-Cl | CH₂=CH | CH₃ | CH₃ | N | |
| 3-Cl | 5-Cl | CH₂=CHCH₂ | CH₃ | CH₃ | N | |
| 3-Cl | 5-Cl | HC≡C | CH₃ | CH₃ | N | |
| 3-Cl | 5-Cl | CH₃C≡C | CH₃ | CH₃ | N | |
| 3-Cl | 5-Cl | ClCH₂ | CH₃ | CH₃ | N | |
| 3-Cl | 5-Cl | BrCH₂ | CH₃ | CH₃ | N | |
| 3-Cl | 5-Cl | Cl₃C | CH₃ | CH₃ | N | |
| 3-Cl | 5-Cl | Br₃C | CH₃ | CH₃ | N | |
| 3-Cl | 5-Cl | F₃C | CH₃ | CH₃ | N | |
| 3-Cl | 5-Cl | CH₃OCH₂ | CH₃ | CH₃ | N | |
| 3-Cl | 5-Cl | Cl(CH₂)₄ | CH₃ | CH₃ | N | |
| 3-Cl | 5-Cl | ClCH=CH | CH₃ | CH₃ | N | |
| 3-Cl | 5-Cl | ClCH₂CH=CH | CH₃ | CH₃ | N | |
| 3-Cl | 5-Cl |  (cyclopropyl) | CH₃ | CH₃ | N | |
| 3-Cl | 5-Cl |  (cyclopentyl) | CH₃ | CH₃ | CH | |
| 3-Cl | 5-Cl |  (cyclohexyl) | CH₃ | CH₃ | N | |
| 3-Cl | 5-Cl | 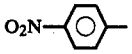 (phenyl) | CH₃ | CH₃ | N | |
| 3-Cl | 5-Cl | O₂N—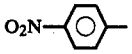— | CH₃ | CH₃ | N | |

TABLE III-continued

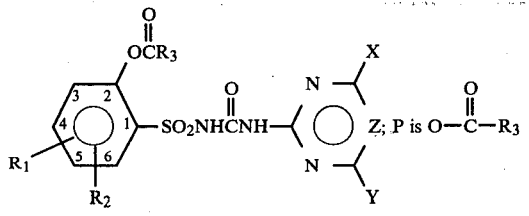

| R₁ | R₂ | R₃ | X | Y | Z | m.p. (°C.) |
|---|---|---|---|---|---|---|
| 3-Cl | 5-Cl | 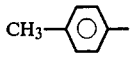 | CH₃ | CH₃ | N | |
| 3-Cl | 5-Cl |  | CH₃ | CH₃ | N | |
| 3-Cl | 5-Cl | 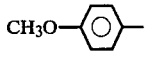 | CH₃ | CH₃ | N | |
| 3-Cl | 5-Cl | 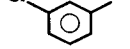 | CH₃ | CH₃ | N | |
| 3-Cl | 5-Cl | 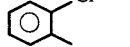 | CH₃ | CH₃ | N | |
| 3-Cl | 5-Cl | 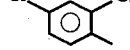 | CH₃ | CH₃ | N | |
| 3-Cl | 5-Cl | H | CH₃O | CH₃ | N | |
| 3-Cl | 5-Cl | CH₃ | CH₃O | CH₃ | N | |
| 3-Cl | 5-Cl | CH₃(CH₂)₄ | CH₃O | CH₃ | N | |
| 3-Cl | 5-Cl | CH₂=CH | CH₃O | CH₃ | N | |
| 3-Cl | 5-Cl | CH₂=CHCH₂ | CH₃O | CH₃ | N | |
| 3-Cl | 5-Cl | HC≡C | CH₃O | CH₃ | N | |
| 3-Cl | 5-Cl | CH₃C≡C | CH₃O | CH₃ | N | |
| 3-Cl | 5-Cl | ClCH₂ | CH₃O | CH₃ | N | |
| 3-Cl | 5-Cl | BrCH₂ | CH₃O | CH₃ | N | |
| 3-Cl | 5-Cl | Cl₃C | CH₃O | CH₃ | N | |
| 3-Cl | 5-Cl | Br₃C | CH₃O | CH₃ | N | |
| 3-Cl | 5-Cl | F₃C | CH₃O | CH₃ | N | |
| 3-Cl | 5-Cl | CH₃OCH₂ | CH₃O | CH₃ | N | |
| 3-Cl | 5-Cl | Cl(CH₂)₄ | CH₃O | CH₃ | N | |
| 3-Cl | 5-Cl | ClCH=CH | CH₃O | CH₃ | N | |
| 3-Cl | 5-Cl | ClCH₂CH=CH | CH₃O | CH₃ | N | |
| 3-Cl | 5-Cl |  | CH₃O | CH₃ | N | |
| 3-Cl | 5-Cl |  | CH₃O | CH₃ | N | |
| 3-Cl | 5-Cl |  | CH₃O | CH₃ | N | |
| 3-Cl | 5-Cl |  | CH₃O | CH₃ | N | |
| 3-Cl | 5-Cl |  | CH₃O | CH₃ | N | |
| 3-Cl | 5-Cl | 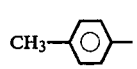 | CH₃O | CH₃ | N | |
| 3-Cl | 5-Cl |  | CH₃O | CH₃ | N | |

TABLE III-continued

| R₁ | R₂ | R₃ | X | Y | Z | m.p. (°C.) |
|---|---|---|---|---|---|---|
| 3-Cl | 5-Cl |  CH₃O—⌬— | CH₃O | CH₃ | N | |
| 3-Cl | 5-Cl |  Cl on 3-methylphenyl | CH₃O | CH₃ | N | |
| 3-Cl | 5-Cl |  Cl on 2-methylphenyl | CH₃O | CH₃ | N | |
| 3-Cl | 5-Cl |  Cl,Cl-dimethylphenyl | CH₃O | CH₃ | N | |
| 3-Cl | 5-Cl | H | CH₃O | CH₃O | N | |
| 3-Cl | 5-Cl | CH₃ | CH₃O | CH₃O | N | |
| 3-Cl | 5-Cl | CH₃(CH₂)₄ | CH₃O | CH₃O | N | |
| 3-Cl | 5-Cl | CH₂=CH | CH₃O | CH₃O | N | |
| 3-Cl | 5-Cl | CH₂=CHCH₂ | CH₃O | CH₃O | N | |
| 3-Cl | 5-Cl | HC≡C | CH₃O | CH₃O | N | |
| 3-Cl | 5-Cl | CH₃C≡C | CH₃O | CH₃O | N | |
| 3-Cl | 5-Cl | ClCH₂ | CH₃O | CH₃O | N | |
| 3-Cl | 5-Cl | BrCH₂ | CH₃O | CH₃O | N | |
| 3-Cl | 5-Cl | Cl₃C | CH₃O | CH₃O | N | |
| 3-Cl | 5-Cl | Br₃C | CH₃O | CH₃O | N | |
| 3-Cl | 5-Cl | F₃C | CH₃O | CH₃O | N | |
| 3-Cl | 5-Cl | CH₃OCH₂ | CH₃O | CH₃O | N | |
| 3-Cl | 5-Cl | Cl(CH₂)₄ | CH₃O | CH₃O | N | |
| 3-Cl | 5-Cl | ClCH=CH | CH₃O | CH₃O | N | |
| 3-Cl | 5-Cl | ClCH₂CH=CH | CH₃O | CH₃O | N | |
| 3-Cl | 5-Cl |  cyclopropyl | CH₃O | CH₃O | N | |
| 3-Cl | 5-Cl |  cyclopentyl | CH₃O | CH₃O | N | |
| 3-Cl | 5-Cl |  cyclohexyl | CH₃O | CH₃O | N | |
| 3-Cl | 5-Cl |  phenyl | CH₃O | CH₃O | N | |
| 3-Cl | 5-Cl | O₂N—⌬—  | CH₃O | CH₃O | N | |
| 3-Cl | 5-Cl | CH₃—⌬—  | CH₃O | CH₃O | N | |
| 3-Cl | 5-Cl | Cl—⌬—  | CH₃O | CH₃O | N | |
| 3-Cl | 5-Cl | CH₃O—⌬— | CH₃O | CH₃O | N | |
| 3-Cl | 5-Cl | Cl—⌬— (3-Cl phenyl)  | CH₃O | CH₃O | N | |

TABLE III-continued

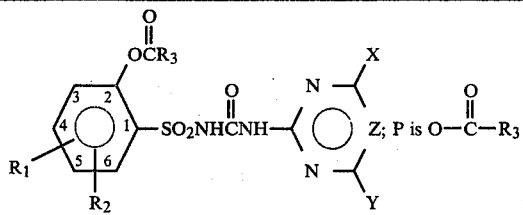

| R₁ | R₂ | R₃ | X | Y | Z | m.p. (°C.) |
|---|---|---|---|---|---|---|
| 3-Cl | 5-Cl | 2-Cl-phenyl | CH₃O | CH₃O | N | |
| 3-Cl | 5-Cl | 2,6-diCl-phenyl | CH₃O | CH₃O | N | |
| 5-F | H | CH₃ | CH₃ | CH₃ | CH | |
| 3-Cl | H | CH₃ | CH₃ | CH₃ | CH | |
| 4-Cl | H | CH₃ | CH₃ | CH₃ | CH | |
| 5-Cl | H | CH₃ | CH₃ | CH₃ | CH | |
| 6-Cl | H | CH₃ | CH₃ | CH₃ | CH | |
| 5-Br | H | CH₃ | CH₃ | CH₃ | CH | |
| 3-CH₃ | H | CH₃ | CH₃ | CH₃ | CH | |
| 6-CH₃ | H | CH₃ | CH₃ | CH₃ | CH | |
| 6-(CH₃)₂CH | H | CH₃ | CH₃ | CH₃ | CH | |
| 5-NO₂ | H | CH₃ | CH₃ | CH₃ | CH | |
| 5-CH₃O | H | CH₃ | CH₃ | CH₃ | CH | |
| 5-(CH₃)₂CHO | H | CH₃ | CH₃ | CH₃ | CH | |
| 5-CF₃ | H | CH₃ | CH₃ | CH₃ | CH | |
| 5-OCOCH₃ | H | CH₃ | CH₃ | CH₃ | CH | |
| 3-CH₃ | 5-CH₃ | CH₃ | CH₃ | CH₃ | CH | |
| 3-Cl | 5-CH₃ | CH₃ | CH₃ | CH₃ | CH | |
| 5-F | H | CH₃ | CH₃O | CH₃ | CH | |
| 3-Cl | H | CH₃ | CH₃O | CH₃ | CH | |
| 4-Cl | H | CH₃ | CH₃O | CH₃ | CH | |
| 5-Cl | H | CH₃ | CH₃O | CH₃ | CH | |
| 6-Cl | H | CH₃ | CH₃O | CH₃ | CH | |
| 5-Br | H | CH₃ | CH₃O | CH₃ | CH | |
| 3-CH₃ | H | CH₃ | CH₃O | CH₃ | CH | |
| 6-CH₃ | H | CH₃ | CH₃O | CH₃ | CH | |
| 6-(CH₃)₂CH | H | CH₃ | CH₃O | CH₃ | CH | |
| 5-NO₂ | H | CH₃ | CH₃O | CH₃ | CH | |
| 5-CH₃O | H | CH₃ | CH₃O | CH₃ | CH | |
| 5-(CH₃)₂CHO | H | CH₃ | CH₃O | CH₃ | CH | |
| 5-CF₃ | H | CH₃ | CH₃ | CH₃ | CH | |
| 5-OCOCH₃ | H | CH₃ | CH₃O | CH₃ | CH | |
| 3-CH₃ | 5-CH₃ | CH₃ | CH₃O | CH₃ | CH | |
| 3-Cl | 5-CH₃ | CH₃ | CH₃O | CH₃ | CH | |
| 5-F | H | CH₃ | CH₃O | CH₃O | CH | |
| 3-Cl | H | CH₃ | CH₃O | CH₃O | CH | |
| 4-Cl | H | CH₃ | CH₃O | CH₃O | CH | |
| 5-Cl | H | CH₃ | CH₃O | CH₃O | CH | |
| 6-Cl | H | CH₃ | CH₃O | CH₃O | CH | |
| 5-Br | H | CH₃ | CH₃O | CH₃O | CH | |
| 3-CH₃ | H | CH₃ | CH₃O | CH₃O | CH | |
| 6-CH₃ | H | CH₃ | CH₃O | CH₃O | CH | |
| 6-(CH₃)₂CH | H | CH₃ | CH₃O | CH₃O | CH | |
| 5-NO₂ | H | CH₃ | CH₃O | CH₃O | CH | |
| 5-CH₃O | H | CH₃ | CH₃O | CH₃O | CH | |
| 5-(CH₃)₂CHO | H | CH₃ | CH₃O | CH₃O | CH | |
| 5-CF₃ | H | CH₃ | CH₃O | CH₃O | CH | |
| 5-OCOCH₃ | H | CH₃ | CH₃O | CH₃O | CH | |
| 3-CH₃ | 5-CH₃ | CH₃ | CH₃O | CH₃O | CH | |
| 3-Cl | 5-CH₃ | CH₃ | CH₃O | CH₃O | CH | |
| 5-F | H | CH₃ | CH₃ | CH₃ | N | |
| 3-Cl | H | CH₃ | CH₃ | CH₃ | N | |
| 4-Cl | H | CH₃ | CH₃ | CH₃ | N | |
| 5-Cl | H | CH₃ | CH₃ | CH₃ | N | |
| 6-Cl | H | CH₃ | CH₃ | CH₃ | N | |
| 5-Br | H | CH₃ | CH₃ | CH₃ | N | |
| 3-CH₃ | H | CH₃ | CH₃ | CH₃ | N | |
| 6-CH₃ | H | CH₃ | CH₃ | CH₃ | N | |
| 6-(CH₃)₂CH | H | CH₃ | CH₃ | CH₃ | N | |
| 5-NO₂ | H | CH₃ | CH₃ | CH₃ | N | |
| 5-CH₃O | H | CH₃ | CH₃ | CH₃ | N | |
| 5-(CH₃)₂CHO | H | CH₃ | CH₃ | CH₃ | N | |
| 5-CF₃ | H | CH₃ | CH₃ | CH₃ | N | |
| 5-OCOCH₃ | H | CH₃ | CH₃ | CH₃ | N | |

TABLE III-continued

Structure: aryl ring with OC(O)R₃ at position 2, SO₂NHC(O)NH linker to a heterocyclic ring with substituents X and Y and ring atom Z; P is O—C(O)—R₃

| R₁ | R₂ | R₃ | X | Y | Z | m.p. (°C.) |
|---|---|---|---|---|---|---|
| 3-CH₃ | 5-CH₃ | CH₃ | CH₃ | CH₃ | N | |
| 3-Cl | 5-CH₃ | CH₃ | CH₃ | CH₃ | N | |
| 5-F | H | CH₃ | CH₃O | CH₃ | N | |
| 3-Cl | H | CH₃ | CH₃O | CH₃ | N | |
| 4-Cl | H | CH₃ | CH₃O | CH₃ | N | |
| 5-Cl | H | CH₃ | CH₃O | CH₃ | N | |
| 6-Cl | H | CH₃ | CH₃O | CH₃ | N | |
| 5-Br | H | CH₃ | CH₃O | CH₃ | N | |
| 3-CH₃ | H | CH₃ | CH₃O | CH₃ | N | |
| 6-CH₃ | H | CH₃ | CH₃O | CH₃ | N | |
| 6-(CH₃)₂CH | H | CH₃ | CH₃O | CH₃ | N | |
| 5-NO₂ | H | CH₃ | CH₃O | CH₃ | N | |
| 5-CH₃O | H | CH₃ | CH₃O | CH₃ | N | |
| 5-(CH₃)₂CHO | H | CH₃ | CH₃O | CH₃ | N | |
| 5-CF₃ | H | CH₃ | CH₃O | CH₃ | N | |
| 5-OCOCH₃ | H | CH₃ | CH₃O | CH₃ | N | |
| 3-CH₃ | 5-CH₃ | CH₃ | CH₃O | CH₃ | N | |
| 3-Cl | 5-CH₃ | CH₃ | CH₃O | CH₃ | N | |
| 5-F | H | CH₃ | CH₃O | CH₃O | N | |
| 3-Cl | H | CH₃ | CH₃O | CH₃O | N | |
| 4-Cl | H | CH₃ | CH₃O | CH₃O | N | |
| 5-Cl | H | CH₃ | CH₃O | CH₃O | N | |
| 6-Cl | H | CH₃ | CH₃O | CH₃O | N | |
| 5-Br | H | CH₃ | CH₃O | CH₃O | N | |
| 3-CH₃ | H | CH₃ | CH₃O | CH₃O | N | |
| 6-CH₃ | H | CH₃ | CH₃O | CH₃O | N | |
| 6-(CH₃)₂CH | H | CH₃ | CH₃O | CH₃O | N | |
| 5-NO₂ | H | CH₃ | CH₃O | CH₃O | N | |
| 5-CH₃O | H | CH₃ | CH₃O | CH₃O | N | |
| 5-(CH₃)₂CHO | H | CH₃ | CH₃O | CH₃O | N | |
| 5-CF₃ | H | CH₃ | CH₃O | CH₃O | N | |
| 5-OCOCH₃ | H | CH₃ | CH₃O | CH₃O | N | |
| 3-CH₃ | 5-CH₃ | CH₃ | CH₃O | CH₃O | N | |
| 3-Cl | 5-CH₃ | CH₃ | CH₃O | CH₃O | N | |
| H | H | CH₃ | CH₃ | CH₃ | CCl | |
| H | H | CH₃ | CH₃ | CH₃ | CBr | |
| H | H | CH₃ | CH₃ | CH₃ | CCN | |
| H | H | CH₃ | CH₃ | CH₃ | CCH₃ | |
| H | H | CH₃ | CH₃ | CH₃ | CC₂H₅ | |
| H | H | CH₃ | CH₃ | CH₃ | CCH₂CH₂Cl | |
| H | H | CH₃ | CH₃ | CH₃ | CCH₂CH₂CN | |
| Cl | Cl | CH₃ | CH₃ | CH₃ | CCl | |
| Cl | Cl | CH₃ | CH₃ | CH₃ | CBr | |
| Cl | Cl | CH₃ | CH₃ | CH₃ | CCN | |
| Cl | Cl | CH₃ | CH₃ | CH₃ | CCH₃ | |
| Cl | Cl | CH₃ | CH₃ | CH₃ | CC₂H₅ | |
| Cl | Cl | CH₃ | CH₃ | CH₃ | CCH₂CH₂Cl | |
| Cl | Cl | CH₃ | CH₃ | CH₃ | CCH₂CH₂CN | |
| H | H | CH₃ | H | CH₃ | CH | |
| H | H | CH₃ | Cl | CH₃ | CH | |
| H | H | CH₃ | Br | CH₃ | CH | |
| H | H | CH₃ | C₂H₅ | CH₃ | CH | |
| H | H | CH₃ | CH₃(CH₂)₂O | CH₃ | CH | |
| H | H | CH₃ | CF₃ | CH₃ | CH | |
| H | H | CH₃ | CH₃S | CH₃ | CH | |
| H | H | CH₃ | CH₃OCH₂ | CH₃ | CH | |
| 3-Cl | 5-Cl | CH₃ | H | CH₃ | CH | |
| 3-Cl | 5-Cl | CH₃ | Cl | CH₃ | CH | |
| 3-Cl | 5-Cl | CH₃ | Br | CH₃ | CH | |
| 3-Cl | 5-Cl | CH₃ | C₂H₅ | CH₃ | CH | |
| 3-Cl | 5-Cl | CH₃ | CH₃(CH₂)₂O | CH₃ | CH | |
| 3-Cl | 5-Cl | CH₃ | CF₃ | CH₃ | CH | |
| 3-Cl | 5-Cl | CH₃ | CH₃S | CH₃ | CH | |
| 3-Cl | 5-Cl | CH₃ | CH₃OCH₂ | CH₃ | CH | |

TABLE IV

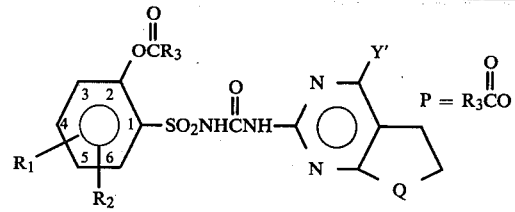

| R₁ | R₂ | R₃ | Y' | Q |
|---|---|---|---|---|
| 3-Cl | 5-Cl | CH₃ | H | O |
| 3-Cl | 5-Cl | CH₃ | CH₃ | O |
| 3-Cl | 5-Cl | CH₃ | OCH₃ | O |
| 3-Cl | 5-Cl | CH₃ | Cl | O |
| 3-Cl | 5-Cl | CH₃ | H | CH₂ |
| 3-Cl | 5-Cl | CH₃ | CH₃ | CH₂ |
| 3-Cl | 5-Cl | CH₃ | OCH₃ | CH₂ |
| 3-Cl | 5-Cl | CH₃ | Cl | CH₂ |
| H | H | CH₃ | H | O |

TABLE IV-continued

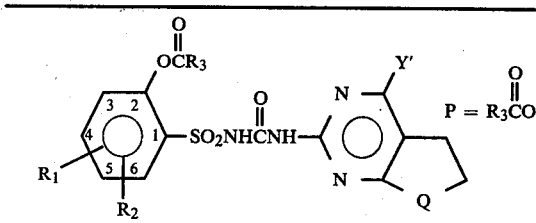

| R₁ | R₂ | R₃ | Y' | Q |
|---|---|---|---|---|
| H | H | CH₃ | CH₃ | O |
| H | H | CH₃ | OCH₃ | O |
| H | H | CH₃ | Cl | O |
| H | H | CH₃ | H | CH₂ |
| H | H | CH₃ | CH₃ | CH₂ |
| H | H | CH₃ | OCH₃ | CH₂ |
| H | H | CH₃ | Cl | CH₂ |

TABLE V

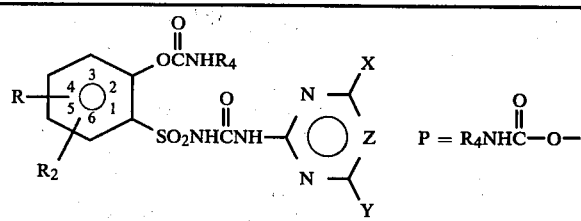

| R₁ | R₂ | R₄ | X | Y | Z |
|---|---|---|---|---|---|
| H | H | CH₃ | CH₃ | CH₃ | CH |
| H | H | CH₃(CH₂)₅ | CH₃ | CH₃ | CH |
| H | H | CH₂=CHCH₂ | CH₃ | CH₃ | CH |
| H | H | CH₃CH=CHCH₂ | CH₃ | CH₃ | CH |
| H | H | cyclopropyl | CH₃ | CH₃ | CH |
| H | H | cyclopentyl | CH₃ | CH₃ | CH |
| H | H | cyclohexyl | CH₃ | CH₃ | CH |
| H | H | methylcyclopentyl | CH₃ | CH₃ | CH |
| H | H | methylcyclohexyl | CH₃ | CH₃ | CH |
| H | H | phenyl | CH₃ | CH₃ | CH |
| H | H | 4-F-phenyl | CH₃ | CH₃ | CH |
| H | H | 4-Cl-phenyl | CH₃ | CH₃ | CH |
| H | H | 4-Br-phenyl | CH₃ | CH₃ | CH |
| H | H | 4-CH₃-phenyl | CH₃ | CH₃ | CH |

TABLE V-continued

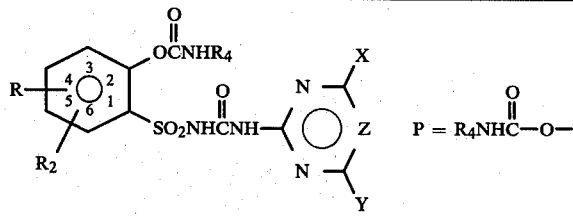

P = R₄NHC(O)—O—

| R₁ | R₂ | R₄ | X | Y | Z |
|---|---|---|---|---|---|
| H | H | (CH₃)₂CH—C₆H₄— | CH₃ | CH₃ | CH |
| H | H | O₂N—C₆H₄— | CH₃ | CH₃ | CH |
| H | H | NC—C₆H₄— | CH₃ | CH₃ | CH |
| H | H | CH₃SO₂—C₆H₄— | CH₃ | CH₃ | CH |
| H | H | CH₃O—C₆H₄— | CH₃ | CH₃ | CH |
| H | H | CH₃S—C₆H₄— | CH₃ | CH₃ | CH |
| H | H | CF₃—C₆H₄— | CH₃ | CH₃ | CH |
| H | H | Cl-C₆H₄— (m) | CH₃ | CH₃ | CH |
| H | H | Cl-C₆H₄— (o) | CH₃ | CH₃ | CH |
| H | H | Cl,CH₃-C₆H₃— | CH₃ | CH₃ | CH |
| H | H | Cl,(CH₃)₂CH-C₆H₃— | CH₃ | CH₃ | CH |
| H | H | Cl,Cl-C₆H₃— | CH₃ | CH₃ | CH |
| H | H | C₆H₅—CH₂ | CH₃ | CH₃ | CH |
| H | H | CH₃—C₆H₄—CH₂ | CH₃ | CH₃ | CH |
| H | H | (CH₃)₂CH—C₆H₄—CH₂ | CH₃ | CH₃ | CH |
| H | H | CH₃ | CH₃ | CH₃O | CH |
| H | H | CH₃(CH₂)₅ | CH₃ | CH₃O | CH |
| H | H | CH₂=CHCH₂ | CH₃ | CH₃O | CH |
| H | H | CH₃CH=CHCH₂ | CH₃ | CH₃O | CH |

TABLE V-continued

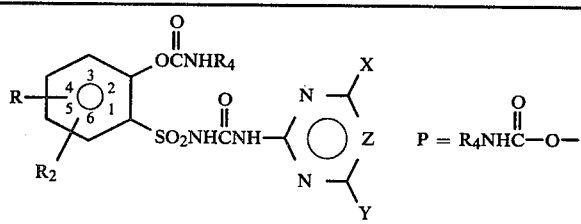

| R₁ | R₂ | R₄ | X | Y | Z |
|----|----|----|----|----|----|
| H | H | cyclopropyl | CH₃ | CH₃O | CH |
| H | H | cyclopentyl | CH₃ | CH₃O | CH |
| H | H | cyclohexyl | CH₃ | CH₃O | CH |
| H | H | 1,2-dimethylcyclopentyl | CH₃ | CH₃O | CH |
| H | H | 1,2-dimethylcyclohexyl | CH₃ | CH₃O | CH |
| H | H | phenyl | CH₃ | CH₃O | CH |
| H | H | 4-F-phenyl | CH₃ | CH₃O | CH |
| H | H | 4-Cl-phenyl | CH₃ | CH₃O | CH |
| H | H | 4-Br-phenyl | CH₃ | CH₃O | CH |
| H | H | 4-CH₃-phenyl | CH₃ | CH₃O | CH |
| H | H | 4-(CH₃)₂CH-phenyl | CH₃ | CH₃O | CH |
| H | H | 4-O₂N-phenyl | CH₃ | CH₃O | CH |
| H | H | 4-NC-phenyl | CH₃ | CH₃O | CH |
| H | H | 4-CH₃SO₂-phenyl | CH₃ | CH₃O | CH |
| H | H | 4-CH₃O-phenyl | CH₃ | CH₃O | CH |
| H | H | 4-CH₃S-phenyl | CH₃ | CH₃O | CH |
| H | H | 4-CF₃-phenyl | CH₃ | CH₃O | CH |

TABLE V-continued

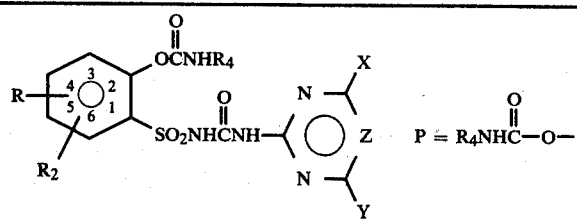

| $R_1$ | $R_2$ | $R_4$ | X | Y | Z |
|---|---|---|---|---|---|
| H | H | 3-Cl-phenyl | $CH_3$ | $CH_3O$ | CH |
| H | H | 2-Cl-phenyl | $CH_3$ | $CH_3O$ | CH |
| H | H | 2-Cl-5-CH$_3$-phenyl | $CH_3$ | $CH_3O$ | CH |
| H | H | 2-Cl-5-(CH$_3$)$_2$CH-phenyl | $CH_3$ | $CH_3O$ | CH |
| H | H | 2,5-diCl-phenyl | $CH_3$ | $CH_3O$ | CH |
| H | H | benzyl | $CH_3$ | $CH_3O$ | CH |
| H | H | 4-CH$_3$-benzyl | $CH_3$ | $CH_3O$ | CH |
| H | H | 4-(CH$_3$)$_2$CH-benzyl | $CH_3$ | $CH_3O$ | CH |
| H | H | $CH_3$ | $CH_3O$ | $CH_3O$ | CH |
| H | H | $CH_3(CH_2)_5$ | $CH_3O$ | $CH_3O$ | CH |
| H | H | $CH_2=CHCH_2$ | $CH_3O$ | $CH_3O$ | CH |
| H | H | $CH_3CH=CHCH_2$ | $CH_3O$ | $CH_3O$ | CH |
| H | H | cyclopropyl | $CH_3O$ | $CH_3O$ | CH |
| H | H | cyclopentyl | $CH_3O$ | $CH_3O$ | CH |
| H | H | cyclohexyl | $CH_3O$ | $CH_3O$ | CH |
| H | H | 2-CH$_3$-cyclopentyl | $CH_3O$ | $CH_3O$ | CH |
| H | H | 2-CH$_3$-cyclohexyl | $CH_3O$ | $CH_3O$ | CH |
| H | H | phenyl | $CH_3O$ | $CH_3O$ | CH |
| H | H | 4-F-phenyl | $CH_3O$ | $CH_3O$ | CH |

TABLE V-continued

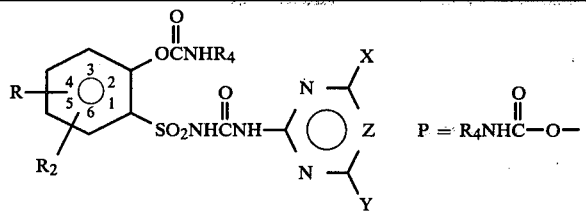

| R₁ | R₂ | R₄ | X | Y | Z |
|---|---|---|---|---|---|
| H | H | Cl—⌬— | CH₃O | CH₃O | CH |
| H | H | Br—⌬— | CH₃O | CH₃O | CH |
| H | H | CH₃—⌬— | CH₃O | CH₃O | CH |
| H | H | (CH₃)₂CH—⌬— | CH₃O | CH₃O | CH |
| H | H | O₂N—⌬— | CH₃O | CH₃O | CH |
| H | H | NC—⌬— | CH₃O | CH₃O | CH |
| H | H | CH₃SO₂—⌬— | CH₃O | CH₃O | CH |
| H | H | CH₃O—⌬— | CH₃O | CH₃O | CH |
| H | H | CH₃S—⌬— | CH₃O | CH₃O | CH |
| H | H | CF₃—⌬— | CH₃O | CH₃O | CH |
| H | H | 2-Cl-C₆H₄- | CH₃O | CH₃O | CH |
| H | H | 2-Cl-C₆H₄- | CH₃O | CH₃O | CH |
| H | H | 2-Cl-4-CH₃-C₆H₃- | CH₃O | CH₃O | CH |
| H | H | 2-Cl-4-(CH₃)₂CH-C₆H₃- | CH₃O | CH₃O | CH |
| H | H | 2,4-Cl₂-C₆H₃- | CH₃O | CH₃O | CH |
| H | H | C₆H₅CH₂- | CH₃O | CH₃O | CH |

TABLE V-continued

Structure: R₁ and R₂ substituted cyclohexane with OC(=O)NHR₄ at position 2 and SO₂NHC(=O)NH-pyrimidine/triazine substituent; P = R₄NHC(=O)—O—

| R₁ | R₂ | R₄ | X | Y | Z |
|---|---|---|---|---|---|
| H | H | CH₃-C₆H₄-CH₂ | CH₃O | CH₃O | CH |
| H | H | (CH₃)₂CH-C₆H₄-CH₂ | CH₃O | CH₃O | CH |
| H | H | CH₃ | CH₃ | CH₃ | N |
| H | H | CH₃(CH₂)₅ | CH₃ | CH₃ | N |
| H | H | CH₂=CHCH₂ | CH₃ | CH₃ | N |
| H | H | CH₃CH=CHCH₂ | CH₃ | CH₃ | N |
| H | H | cyclopropyl | CH₃ | CH₃ | N |
| H | H | cyclopentyl | CH₃ | CH₃ | N |
| H | H | cyclohexyl | CH₃ | CH₃ | N |
| H | H | 1,2-dimethylcyclopentyl | CH₃ | CH₃ | N |
| H | H | 1,2-dimethylcyclohexyl | CH₃ | CH₃ | N |
| H | H | phenyl | CH₃ | CH₃ | N |
| H | H | F-C₆H₄- | CH₃ | CH₃ | N |
| H | H | Cl-C₆H₄- | CH₃ | CH₃ | N |
| H | H | Br-C₆H₄- | CH₃ | CH₃ | N |
| H | H | CH₃-C₆H₄- | CH₃ | CH₃ | N |
| H | H | (CH₃)₂CH-C₆H₄- | CH₃ | CH₃ | N |
| H | H | O₂N-C₆H₄- | CH₃ | CH₃ | N |
| H | H | NC-C₆H₄- | CH₃ | CH₃ | N |
| H | H | CH₃SO₂-C₆H₄- | CH₃ | CH₃ | N |

TABLE V-continued

Structure: R—[cyclohexane with positions 1-6, R₂ at 5, OC(O)NHR₄ at 2, SO₂NHC(O)NH— linked to pyrimidine/triazine ring with X, Y, Z substituents]; P = R₄NHC(O)—O—

| R₁ | R₂ | R₄ | X | Y | Z |
|---|---|---|---|---|---|
| H | H | CH₃O—C₆H₄— (4-methoxyphenyl) | CH₃ | CH₃ | N |
| H | H | CH₃S—C₆H₄— (4-methylthiophenyl) | CH₃ | CH₃ | N |
| H | H | CF₃—C₆H₄— (4-trifluoromethylphenyl) | CH₃ | CH₃ | N |
| H | H | 3-Cl-C₆H₄— | CH₃ | CH₃ | N |
| H | H | 2-Cl-C₆H₄— | CH₃ | CH₃ | N |
| H | H | 2-Cl-4-CH₃-C₆H₃— | CH₃ | CH₃ | N |
| H | H | 2-Cl-4-(CH₃)₂CH-C₆H₃— | CH₃ | CH₃ | N |
| H | H | 2,3-Cl₂-C₆H₃— | CH₃ | CH₃ | N |
| H | H | C₆H₅—CH₂— | CH₃ | CH₃ | N |
| H | H | CH₃—C₆H₄—CH₂— | CH₃ | CH₃ | N |
| H | H | (CH₃)₂CH—C₆H₄—CH₂— | CH₃ | CH₃ | N |
| H | H | CH₃ | CH₃O | CH₃ | N |
| H | H | CH₃(CH₂)₅ | CH₃O | CH₃ | N |
| H | H | CH₂=CHCH₂ | CH₃O | CH₃ | N |
| H | H | CH₃CH=CHCH₂ | CH₃O | CH₃ | N |
| H | H | cyclopropyl | CH₃O | CH₃ | N |
| H | H | cyclopentyl | CH₃O | CH₃ | N |
| H | H | cyclohexyl | CH₃O | CH₃ | N |
| H | H | 2-methylcyclopentyl | CH₃O | CH₃ | N |

TABLE V-continued
        P = R₄NHC—O—
| R₁ | R₂ | R₄ | X | Y | Z |
|---|---|---|---|---|---|
| H | H |  (2-methylcyclohexyl) | CH₃O | CH₃ | N |
| H | H |  (phenyl) | CH₃O | CH₃ | N |
| H | H | F—— | CH₃O | CH₃ | N |
| H | H | Cl—— | CH₃O | CH₃ | N |
| H | H | Br—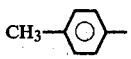— | CH₃O | CH₃ | N |
| H | H | CH₃—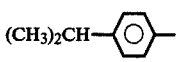— | CH₃O | CH₃ | N |
| H | H | (CH₃)₂CH—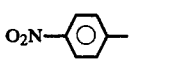— | CH₃O | CH₃ | N |
| H | H | O₂N—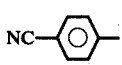— | CH₃O | CH₃ | N |
| H | H | NC—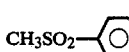— | CH₃O | CH₃ | N |
| H | H | CH₃SO₂—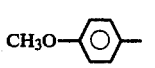— | CH₃O | CH₃ | N |
| H | H | CH₃O—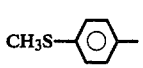— | CH₃O | CH₃ | N |
| H | H | CH₃S—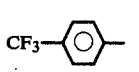— | CH₃O | CH₃ | N |
| H | H | CF₃—— | CH₃O | CH₃ | N |
| H | H |  (3-Cl-phenyl) | CH₃O | CH₃ | N |
| H | H |  (2-Cl-phenyl) | CH₃O | CH₃ | N |
| H | H | 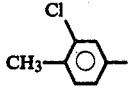 (Cl, CH₃-phenyl) | CH₃O | CH₃ | N |

TABLE V-continued

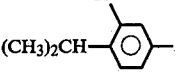

| R₁ | R₂ | R₄ | X | Y | Z |
|---|---|---|---|---|---|
| H | H | Cl—⟨phenyl⟩— with (CH₃)₂CH— | CH₃O | CH₃ | N |
| H | H | Cl,Cl—⟨phenyl⟩— | CH₃O | CH₃ | N |
| H | H | ⟨phenyl⟩—CH₂ | CH₃O | CH₃ | N |
| H | H | CH₃—⟨phenyl⟩—CH₂ | CH₃O | CH₃ | N |
| H | H | (CH₃)₂CH—⟨phenyl⟩—CH₂ | CH₃O | CH₃ | N |
| H | H | CH₃ | CH₃O | CH₃O | N |
| H | H | CH₃(CH₂)₅ | CH₃O | CH₃O | N |
| H | H | CH₂=CHCH₂ | CH₃O | CH₃O | N |
| H | H | CH₃CH=CHCH₂ | CH₃O | CH₃O | N |
| H | H | ▵ (cyclopropyl) | CH₃O | CH₃O | N |
| H | H | ⬠ (cyclopentyl) | CH₃O | CH₃O | N |
| H | H | ⬡ (cyclohexyl) | CH₃O | CH₃O | N |
| H | H | 2,5-dimethylcyclopentyl | CH₃O | CH₃O | N |
| H | H | methylcyclohexyl-CH₃ | CH₃O | CH₃O | N |
| H | H | ⟨phenyl⟩ | CH₃O | CH₃O | N |
| H | H | F—⟨phenyl⟩— | CH₃O | CH₃O | N |
| H | H | Cl—⟨phenyl⟩— | CH₃O | CH₃O | N |
| H | H | Br—⟨phenyl⟩— | CH₃O | CH₃O | N |
| H | H | CH₃—⟨phenyl⟩— | CH₃O | CH₃O | N |
| H | H | (CH₃)₂CH—⟨phenyl⟩— | CH₃O | CH₃O | N |

TABLE V-continued

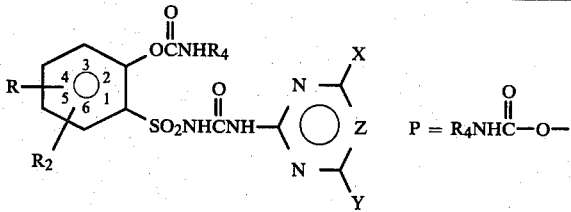

| R₁ | R₂ | R₄ | X | Y | Z |
|---|---|---|---|---|---|
| H | H | O₂N—⌬— | CH₃O | CH₃O | N |
| H | H | NC—⌬— | CH₃O | CH₃O | N |
| H | H | CH₃SO₂—⌬— | CH₃O | CH₃O | N |
| H | H | CH₃O—⌬— | CH₃O | CH₃O | N |
| H | H | CH₃S—⌬— | CH₃O | CH₃O | N |
| H | H | CF₃—⌬— | CH₃O | CH₃O | N |
| H | H | 3-Cl-C₆H₄— | CH₃O | CH₃O | N |
| H | H | 2-Cl-C₆H₄— | CH₃O | CH₃O | N |
| H | H | 2-Cl-4-CH₃-C₆H₃— | CH₃O | CH₃O | N |
| H | H | 2-Cl-4-(CH₃)₂CH-C₆H₃— | CH₃O | CH₃O | N |
| H | H | 2,3-Cl₂-C₆H₃— | CH₃O | CH₃O | N |
| H | H | C₆H₅CH₂— | CH₃O | CH₃O | N |
| H | H | 4-CH₃-C₆H₄-CH₂— | CH₃O | CH₃O | N |
| H | H | 4-(CH₃)₂CH-C₆H₄-CH₂— | CH₃O | CH₃O | N |
| 3-Cl | 5-Cl | CH₃ | CH₃ | CH₃ | CH |
| 3-Cl | 5-Cl | CH₃(CH₂)₅ | CH₃ | CH₃ | CH |
| 3-Cl | 5-Cl | CH₂=CHCH₂ | CH₃ | CH₃ | CH |
| 3-Cl | 5-Cl | CH₃CH=CHCH₂ | CH₃ | CH₃ | CH |
| 3-Cl | 5-Cl | △ | CH₃ | CH₃ | CH |

TABLE V-continued $$\underset{R_2}{\overset{R}{\bigcirc}}\overset{\overset{O}{\parallel}}{\underset{SO_2NHCNH}{OCNHR_4}}-\underset{N}{\overset{N}{\bigcirc}}\overset{X}{\underset{Y}{\bigcirc}}Z \qquad P = R_4NH\overset{O}{\overset{\parallel}{C}}-O-$$

| $R_1$ | $R_2$ | $R_4$ | X | Y | Z |
|---|---|---|---|---|---|
| 3-Cl | 5-Cl | cyclopentyl | $CH_3$ | $CH_3$ | CH |
| 3-Cl | 5-Cl | cyclohexyl | $CH_3$ | $CH_3$ | CH |
| 3-Cl | 5-Cl | 2,3-dimethylcyclopentyl | $CH_3$ | $CH_3$ | CH |
| 3-Cl | 5-Cl | 2-methylcyclohexyl | $CH_3$ | $CH_3$ | CH |
| 3-Cl | 5-Cl | phenyl | $CH_3$ | $CH_3$ | CH |
| 3-Cl | 5-Cl | 4-F-phenyl | $CH_3$ | $CH_3$ | CH |
| 3-Cl | 5-Cl | 4-Cl-phenyl | $CH_3$ | $CH_3$ | CH |
| 3-Cl | 5-Cl | 4-Br-phenyl | $CH_3$ | $CH_3$ | CH |
| 3-Cl | 5-Cl | 4-$CH_3$-phenyl | $CH_3$ | $CH_3$ | CH |
| 3-Cl | 5-Cl | 4-$(CH_3)_2CH$-phenyl | $CH_3$ | $CH_3$ | CH |
| 3-Cl | 5-Cl | 4-$O_2N$-phenyl | $CH_3$ | $CH_3$ | CH |
| 3-Cl | 5-Cl | 4-NC-phenyl | $CH_3$ | $CH_3$ | CH |
| 3-Cl | 5-Cl | 4-$CH_3SO_2$-phenyl | $CH_3$ | $CH_3$ | CH |
| 3-Cl | 5-Cl | 4-$CH_3O$-phenyl | $CH_3$ | $CH_3$ | CH |
| 3-Cl | 5-Cl | 4-$CH_3S$-phenyl | $CH_3$ | $CH_3$ | CH |
| 3-Cl | 5-Cl | 4-$CF_3$-phenyl | $CH_3$ | $CH_3$ | CH |

TABLE V-continued

| R₁ | R₂ | R₄ | X | Y | Z |
|---|---|---|---|---|---|
| 3-Cl | 5-Cl |  | CH₃ | CH₃ | CH |
| 3-Cl | 5-Cl | 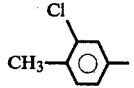 | CH₃ | CH₃ | CH |
| 3-Cl | 5-Cl | 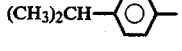 | CH₃ | CH₃ | CH |
| 3-Cl | 5-Cl | 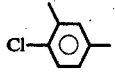 | CH₃ | CH₃ | CH |
| 3-Cl | 5-Cl | 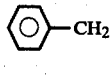 | CH₃ | CH₃ | CH |
| 3-Cl | 5-Cl |  | CH₃ | CH₃ | CH |
| 3-Cl | 5-Cl |  | CH₃ | CH₃ | CH |
| 3-Cl | 5-Cl | 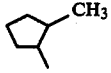 | CH₃ | CH₃ | CH |
| 3-Cl | 5-Cl | CH₃ | CH₃O | CH₃ | CH |
| 3-Cl | 5-Cl | CH₃(CH₂)₅ | CH₃O | CH₃ | CH |
| 3-Cl | 5-Cl | CH₂=CHCH₂ | CH₃O | CH₃ | CH |
| 3-Cl | 5-Cl | CH₃CH=CHCH₂ | CH₃O | CH₃ | CH |
| 3-Cl | 5-Cl | △ | CH₃O | CH₃ | CH |
| 3-Cl | 5-Cl | ⬠ | CH₃O | CH₃ | CH |
| 3-Cl | 5-Cl | ⬡ | CH₃O | CH₃ | CH |
| 3-Cl | 5-Cl |  | CH₃O | CH₃ | CH |
| 3-Cl | 5-Cl | (cyclohexyl-CH₃) | CH₃O | CH₃ | CH |
| 3-Cl | 5-Cl | (phenyl) | CH₃O | CH₃ | CH |

TABLE V-continued

| R₁ | R₂ | R₄ | X | Y | Z |
|---|---|---|---|---|---|
| 3-Cl | 5-Cl | 4-F-C₆H₄- | CH₃O | CH₃ | CH |
| 3-Cl | 5-Cl | 4-Cl-C₆H₄- | CH₃O | CH₃ | CH |
| 3-Cl | 5-Cl | 4-Br-C₆H₄- | CH₃O | CH₃ | CH |
| 3-Cl | 5-Cl | 4-CH₃-C₆H₄- | CH₃O | CH₃ | CH |
| 3-Cl | 5-Cl | 4-(CH₃)₂CH-C₆H₄- | CH₃O | CH₃ | CH |
| 3-Cl | 5-Cl | 4-O₂N-C₆H₄- | CH₃O | CH₃ | CH |
| 3-Cl | 5-Cl | 4-NC-C₆H₄- | CH₃O | CH₃ | CH |
| 3-Cl | 5-Cl | 4-CH₃SO₂-C₆H₄- | CH₃O | CH₃ | CH |
| 3-Cl | 5-Cl | 4-CH₃O-C₆H₄- | CH₃O | CH₃ | CH |
| 3-Cl | 5-Cl | 4-CH₃S-C₆H₄- | CH₃O | CH₃ | CH |
| 3-Cl | 5-Cl | 4-CF₃-C₆H₄- | CH₃O | CH₃ | CH |
| 3-Cl | 5-Cl | 3-Cl-C₆H₄- | CH₃O | CH₃ | CH |
| 3-Cl | 5-Cl | 2-Cl-C₆H₄- | CH₃O | CH₃ | CH |
| 3-Cl | 5-Cl | 2-Cl-4-CH₃-C₆H₃- | CH₃O | CH₃ | CH |
| 3-Cl | 5-Cl | 2-Cl-4-(CH₃)₂CH-C₆H₃- | CH₃O | CH₃ | CH |
| 3-Cl | 5-Cl | 2,3-Cl₂-C₆H₃- | CH₃O | CH₃ | CH |

TABLE V-continued

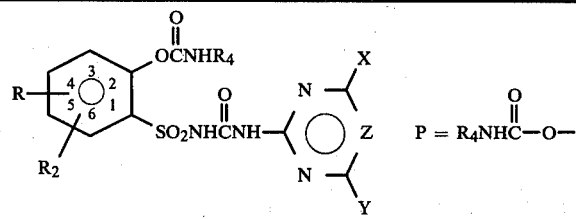

| $R_1$ | $R_2$ | $R_4$ | X | Y | Z |
|---|---|---|---|---|---|
| 3-Cl | 5-Cl | C₆H₅—CH₂ | CH₃O | CH₃ | CH |
| 3-Cl | 5-Cl | CH₃—C₆H₄—CH₂ | CH₃O | CH₃ | CH |
| 3-Cl | 5-Cl | (CH₃)₂CH—C₆H₄—CH₂ | CH₃O | CH₃ | CH |
| 3-Cl | 5-Cl | CH₃ | CH₃O | CH₃O | CH |
| 3-Cl | 5-Cl | CH₃(CH₂)₅ | CH₃O | CH₃O | CH |
| 3-Cl | 5-Cl | CH₂=CHCH₂ | CH₃O | CH₃O | CH |
| 3-Cl | 5-Cl | CH₃CH=CHCH₂ | CH₃O | CH₃O | CH |
| 3-Cl | 5-Cl | cyclopropyl | CH₃O | CH₃O | CH |
| 3-Cl | 5-Cl | cyclopentyl | CH₃O | CH₃O | CH |
| 3-Cl | 5-Cl | cyclohexyl | CH₃O | CH₃O | CH |
| 3-Cl | 5-Cl | 1,2-dimethylcyclopentyl | CH₃O | CH₃O | CH |
| 3-Cl | 5-Cl | 1,2-dimethylcyclohexyl (CH₃ on one position) | CH₃O | CH₃O | CH |
| 3-Cl | 5-Cl | C₆H₅ | CH₃O | CH₃O | CH |
| 3-Cl | 5-Cl | F—C₆H₄— | CH₃O | CH₃O | CH |
| 3-Cl | 5-Cl | Cl—C₆H₄— | CH₃O | CH₃O | CH |
| 3-Cl | 5-Cl | Br—C₆H₄— | CH₃O | CH₃O | CH |
| 3-Cl | 5-Cl | CH₃—C₆H₄— | CH₃O | CH₃O | CH |
| 3-Cl | 5-Cl | (CH₃)₂CH—C₆H₄— | CH₃O | CH₃O | CH |
| 3-Cl | 5-Cl | O₂N—C₆H₄— | CH₃O | CH₃O | CH |
| 3-Cl | 5-Cl | NC—C₆H₄— | CH₃O | CH₃O | CH |

TABLE V-continued

Structure:
- Cyclohexane ring with positions 1-6, R at position 4, R₂ at position 5
- Position 2: OC(=O)NHR₄
- Position 1: SO₂NHCNH-C(=O)-[pyrimidine ring with X, Y, Z substituents]
- Pyrimidine: N, X, Z, Y, N
- P = R₄NHC(=O)—O—

| R₁ | R₂ | R₄ | X | Y | Z |
|---|---|---|---|---|---|
| 3-Cl | 5-Cl | CH₃SO₂—C₆H₄— | CH₃O | CH₃O | CH |
| 3-Cl | 5-Cl | CH₃O—C₆H₄— | CH₃O | CH₃O | CH |
| 3-Cl | 5-Cl | CH₃S—C₆H₄— | CH₃O | CH₃O | CH |
| 3-Cl | 5-Cl | CF₃—C₆H₄— | CH₃O | CH₃O | CH |
| 3-Cl | 5-Cl | 3-Cl-C₆H₄— | CH₃O | CH₃O | CH |
| 3-Cl | 5-Cl | 2-Cl-C₆H₄— | CH₃O | CH₃O | CH |
| 3-Cl | 5-Cl | 2-Cl-3-CH₃-C₆H₃— | CH₃O | CH₃O | CH |
| 3-Cl | 5-Cl | 2-Cl-3-(CH₃)₂CH-C₆H₃— | CH₃O | CH₃O | CH |
| 3-Cl | 5-Cl | 2,3-Cl₂-C₆H₃— | CH₃O | CH₃O | CH |
| 3-Cl | 5-Cl | C₆H₅—CH₂— | CH₃O | CH₃O | CH |
| 3-Cl | 5-Cl | CH₃—C₆H₄—CH₂— | CH₃O | CH₃O | CH |
| 3-Cl | 5-Cl | (CH₃)₂CH—C₆H₄—CH₂— | CH₃O | CH₃O | CH |
| 3-Cl | 5-Cl | CH₃ | CH₃ | CH₃ | N |
| 3-Cl | 5-Cl | CH₃(CH₂)₅ | CH₃ | CH₃ | N |
| 3-Cl | 5-Cl | CH₂=CHCH₂ | CH₃ | CH₃ | N |
| 3-Cl | 5-Cl | CH₃CH=CHCH₂ | CH₃ | CH₃ | N |
| 3-Cl | 5-Cl | cyclopropyl | CH₃ | CH₃ | N |
| 3-Cl | 5-Cl | cyclopentyl | CH₃ | CH₃ | N |
| 3-Cl | 5-Cl | cyclohexyl | CH₃ | CH₃ | N |

TABLE V-continued $$R\underset{R_2}{\overset{4\ 3\ 2}{\underset{5\ 6\ 1}{\bigcirc}}}\overset{\overset{O}{\parallel}}{\underset{SO_2NHCNH}{OCNHR_4}}-\underset{N}{\overset{N}{\underset{\parallel}{\bigcirc}}}\overset{X}{\underset{Y}{\bigcirc}}Z \qquad P = R_4NHC-O-$$

| R₁ | R₂ | R₄ | X | Y | Z |
|---|---|---|---|---|---|
| 3-Cl | 5-Cl | cyclopentyl-CH₃ | CH₃ | CH₃ | N |
| 3-Cl | 5-Cl | cyclohexyl-CH₃ | CH₃ | CH₃ | N |
| 3-Cl | 5-Cl | C₆H₅ | CH₃ | CH₃ | N |
| 3-Cl | 5-Cl | F—C₆H₄— | CH₃ | CH₃ | N |
| 3-Cl | 5-Cl | Cl—C₆H₄— | CH₃ | CH₃ | N |
| 3-Cl | 5-Cl | Br—C₆H₄— | CH₃ | CH₃ | N |
| 3-Cl | 5-Cl | CH₃—C₆H₄— | CH₃ | CH₃ | N |
| 3-Cl | 5-Cl | (CH₃)₂CH—C₆H₄— | CH₃ | CH₃ | N |
| 3-Cl | 5-Cl | O₂N—C₆H₄— | CH₃ | CH₃ | N |
| 3-Cl | 5-Cl | NC—C₆H₄— | CH₃ | CH₃ | N |
| 3-Cl | 5-Cl | CH₃SO₂—C₆H₄— | CH₃ | CH₃ | N |
| 3-Cl | 5-Cl | CH₃O—C₆H₄— | CH₃ | CH₃ | N |
| 3-Cl | 5-Cl | CH₃S—C₆H₄— | CH₃ | CH₃ | N |
| 3-Cl | 5-Cl | CF₃—C₆H₄— | CH₃ | CH₃ | N |
| 3-Cl | 5-Cl | 3-Cl—C₆H₄— | CH₃ | CH₃ | N |
| 3-Cl | 5-Cl | 2-Cl—C₆H₄— | CH₃ | CH₃ | N |

TABLE V-continued $$R \underset{R_2}{\underset{5}{\overset{4}{\bigcirc}}\overset{3}{\underset{6}{\bigcirc}}\overset{2}{\underset{1}{\bigcirc}}} \begin{array}{l} \overset{O}{\text{OCNHR}_4} \\ \text{SO}_2\text{NHCNH} \end{array} \underset{N}{\overset{N}{\bigcirc}} \overset{X}{\underset{Y}{\overset{Z}{\bigcirc}}} \qquad P = R_4\text{NHC}-O-$$

| R₁ | R₂ | R₄ | X | Y | Z |
|---|---|---|---|---|---|
| 3-Cl | 5-Cl | 2-Cl-4-CH₃-phenyl | CH₃ | CH₃ | N |
| 3-Cl | 5-Cl | 2-Cl-4-(CH₃)₂CH-phenyl | CH₃ | CH₃ | N |
| 3-Cl | 5-Cl | 2,3-di-Cl-phenyl | CH₃ | CH₃ | N |
| 3-Cl | 5-Cl | phenyl-CH₂ | CH₃ | CH₃ | N |
| 3-Cl | 5-Cl | 4-CH₃-phenyl-CH₂ | CH₃ | CH₃ | N |
| 3-Cl | 5-Cl | 4-(CH₃)₂CH-phenyl-CH₂ | CH₃ | CH₃ | N |
| 3-Cl | 5-Cl | CH₃ | CH₃O | CH₃ | N |
| 3-Cl | 5-Cl | CH₃(CH₂)₅ | CH₃O | CH₃ | N |
| 3-Cl | 5-Cl | CH₂=CHCH₂ | CH₃O | CH₃ | N |
| 3-Cl | 5-Cl | CH₃CH=CHCH₂ | CH₃O | CH₃ | N |
| 3-Cl | 5-Cl | cyclopropyl | CH₃O | CH₃ | N |
| 3-Cl | 5-Cl | cyclopentyl | CH₃O | CH₃ | N |
| 3-Cl | 5-Cl | cyclohexyl | CH₃O | CH₃ | N |
| 3-Cl | 5-Cl | 2-CH₃-cyclopentyl | CH₃O | CH₃ | N |
| 3-Cl | 5-Cl | 2-CH₃-cyclohexyl | CH₃O | CH₃ | N |
| 3-Cl | 5-Cl | phenyl | CH₃O | CH₃ | N |
| 3-Cl | 5-Cl | 4-F-phenyl | CH₃O | CH₃ | N |
| 3-Cl | 5-Cl | 4-Cl-phenyl | CH₃O | CH₃ | N |
| 3-Cl | 5-Cl | 4-Br-phenyl | CH₃O | CH₃ | N |

TABLE V-continued

Structure:
R—(cyclohexane ring with positions 1-6)—with OC(=O)NHR₄ at position 2 and SO₂NHCNH at position 1; R₂ substituent; connected to pyrimidine ring with X, Y, Z substituents. P = R₄NHC(=O)—O—

| R₁ | R₂ | R₄ | X | Y | Z |
|---|---|---|---|---|---|
| 3-Cl | 5-Cl | CH₃—C₆H₄— | CH₃O | CH₃ | N |
| 3-Cl | 5-Cl | (CH₃)₂CH—C₆H₄— | CH₃O | CH₃ | N |
| 3-Cl | 5-Cl | O₂N—C₆H₄— | CH₃O | CH₃ | N |
| 3-Cl | 5-Cl | NC—C₆H₄— | CH₃O | CH₃ | N |
| 3-Cl | 5-Cl | CH₃SO₂—C₆H₄— | CH₃O | CH₃ | N |
| 3-Cl | 5-Cl | CH₃O—C₆H₄— | CH₃O | CH₃ | N |
| 3-Cl | 5-Cl | CH₃S—C₆H₄— | CH₃O | CH₃ | N |
| 3-Cl | 5-Cl | CF₃—C₆H₄— | CH₃O | CH₃ | N |
| 3-Cl | 5-Cl | 3-Cl-C₆H₄— | CH₃O | CH₃ | N |
| 3-Cl | 5-Cl | 2-Cl-C₆H₄— | CH₃O | CH₃ | N |
| 3-Cl | 5-Cl | (Cl,CH₃)-C₆H₃— | CH₃O | CH₃ | N |
| 3-Cl | 5-Cl | (Cl,(CH₃)₂CH)-C₆H₃— | CH₃O | CH₃ | N |
| 3-Cl | 5-Cl | (Cl,Cl)-C₆H₃— | CH₃O | CH₃ | N |
| 3-Cl | 5-Cl | C₆H₅—CH₂— | CH₃O | CH₃ | N |
| 3-Cl | 5-Cl | CH₃—C₆H₄—CH₂— | CH₃O | CH₃ | N |
| 3-Cl | 5-Cl | (CH₃)₂CH—C₆H₄—CH₂— | CH₃O | CH₃ | N |

TABLE V-continued

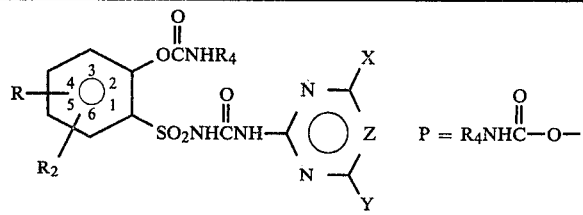

P = R₄NHC(O)—O—

| R₁ | R₂ | R₄ | X | Y | Z |
|---|---|---|---|---|---|
| 3-Cl | 5-Cl | CH₃ | CH₃O | CH₃O | N |
| 3-Cl | 5-Cl | CH₃(CH₂)₅ | CH₃O | CH₃O | N |
| 3-Cl | 5-Cl | CH₂=CHCH₂ | CH₃O | CH₃O | N |
| 3-Cl | 5-Cl | CH₃CH=CHCH₂ | CH₃O | CH₃O | N |
| 3-Cl | 5-Cl | cyclopropyl | CH₃O | CH₃O | N |
| 3-Cl | 5-Cl | cyclopentyl | CH₃O | CH₃O | N |
| 3-Cl | 5-Cl | cyclohexyl | CH₃O | CH₃O | N |
| 3-Cl | 5-Cl | 2-methylcyclopentyl | CH₃O | CH₃O | N |
| 3-Cl | 5-Cl | 2-methylcyclohexyl | CH₃O | CH₃O | N |
| 3-Cl | 5-Cl | C₆H₅ | CH₃O | CH₃O | N |
| 3-Cl | 5-Cl | 4-F-C₆H₄ | CH₃O | CH₃O | N |
| 3-Cl | 5-Cl | 4-Cl-C₆H₄ | CH₃O | CH₃O | N |
| 3-Cl | 5-Cl | 4-Br-C₆H₄ | CH₃O | CH₃O | N |
| 3-Cl | 5-Cl | 4-CH₃-C₆H₄ | CH₃O | CH₃O | N |
| 3-Cl | 5-Cl | 4-(CH₃)₂CH-C₆H₄ | CH₃O | CH₃O | N |
| 3-Cl | 5-Cl | 4-O₂N-C₆H₄ | CH₃O | CH₃O | N |
| 3-Cl | 5-Cl | 4-NC-C₆H₄ | CH₃O | CH₃O | N |
| 3-Cl | 5-Cl | 4-CH₃SO₂-C₆H₄ | CH₃O | CH₃O | N |
| 3-Cl | 5-Cl | 4-CH₃O-C₆H₄ | CH₃O | CH₃O | N |
| 3-Cl | 5-Cl | 4-CH₃S-C₆H₄ | CH₃O | CH₃O | N |

TABLE V-continued

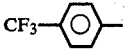

| R₁ | R₂ | R₄ | X | Y | Z |
|---|---|---|---|---|---|
| 3-Cl | 5-Cl | 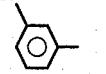 | CH₃O | CH₃O | N |
| 3-Cl | 5-Cl | 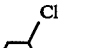 | CH₃O | CH₃O | N |
| 3-Cl | 5-Cl | 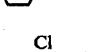 | CH₃O | CH₃O | N |
| 3-Cl | 5-Cl | 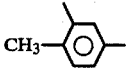 | CH₃O | CH₃O | N |
| 3-Cl | 5-Cl |  | CH₃O | CH₃O | N |
| 3-Cl | 5-Cl |  | CH₃O | CH₃O | N |
| 3-Cl | 5-Cl |  | CH₃O | CH₃O | N |
| 3-Cl | 5-Cl | 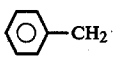 | CH₃O | CH₃O | N |
| 3-Cl | 5-Cl | 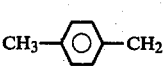 | CH₃O | CH₃O | N |
| 5-F | H | CH₃ | CH₃ | CH₃ | CH |
| 3-Cl | H | CH₃ | CH₃ | CH₃ | CH |
| 4-Cl | H | CH₃ | CH₃ | CH₃ | CH |
| 5-Cl | H | CH₃ | CH₃ | CH₃ | CH |
| 6-Cl | H | CH₃ | CH₃ | CH₃ | CH |
| 5-Br | H | CH₃ | CH₃ | CH₃ | CH |
| 3-CH₃ | H | CH₃ | CH₃ | CH₃ | CH |
| 6-CH₃ | H | CH₃ | CH₃ | CH₃ | CH |
| 6-(CH₃)₂CH | H | CH₃ | CH₃ | CH₃ | CH |
| 5-NO₂ | H | CH₃ | CH₃ | CH₃ | CH |
| 5-CH₃O | H | CH₃ | CH₃ | CH₃ | CH |
| 5-(CH₃)₂CHO | H | CH₃ | CH₃ | CH₃ | CH |
| 5-CF₃ | H | CH₃ | CH₃ | CH₃ | CH |
| 5-OCOCH₃ | H | CH₃ | CH₃ | CH₃ | CH |
| 3-CH₃ | 5-CH₃ | CH₃ | CH₃ | CH₃ | CH |
| 3-Cl | 5-CH₃ | CH₃ | CH₃ | CH₃ | CH |
| 5-F | H | CH₃ | CH₃O | CH₃ | CH |
| 3-Cl | H | CH₃ | CH₃O | CH₃ | CH |
| 4-Cl | H | CH₃ | CH₃O | CH₃ | CH |
| 5-Cl | H | CH₃ | CH₃O | CH₃ | CH |
| 6-Cl | H | CH₃ | CH₃O | CH₃ | CH |
| 5-Br | H | CH₃ | CH₃O | CH₃ | CH |
| 3-CH₃ | H | CH₃ | CH₃O | CH₃ | CH |
| 6-CH₃ | H | CH₃ | CH₃O | CH₃ | CH |
| 6-(CH₃)₂CH | H | CH₃ | CH₃O | CH₃ | CH |
| 5-NO₂ | H | CH₃ | CH₃O | CH₃ | CH |
| 5-CH₃O | H | CH₃ | CH₃O | CH₃ | CH |
| 5-(CH₃)₂CHO | H | CH₃ | CH₃O | CH₃ | CH |

TABLE V-continued

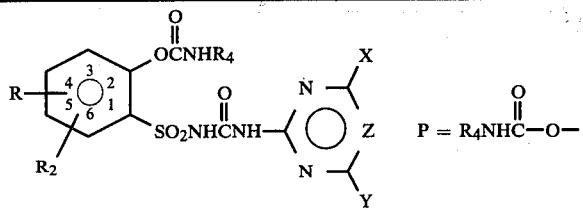

| $R_1$ | $R_2$ | $R_4$ | X | Y | Z |
|---|---|---|---|---|---|
| 5-CF$_3$ | H | CH$_3$ | CH$_3$O | CH$_3$ | CH |
| 5-OCOCH$_3$ | H | CH$_3$ | CH$_3$O | CH$_3$ | CH |
| 3-CH$_3$ | 5-CH$_3$ | CH$_3$ | CH$_3$O | CH$_3$ | CH |
| 3-Cl | 5-CH$_3$ | CH$_3$ | CH$_3$O | CH$_3$ | CH |
| 5-F | H | CH$_3$ | CH$_3$O | CH$_3$O | CH |
| 3-Cl | H | CH$_3$ | CH$_3$O | CH$_3$O | CH |
| 4-Cl | H | CH$_3$ | CH$_3$O | CH$_3$O | CH |
| 5-Cl | H | CH$_3$ | CH$_3$O | CH$_3$O | CH |
| 6-Cl | H | CH$_3$ | CH$_3$O | CH$_3$O | CH |
| 5-Br | H | CH$_3$ | CH$_3$O | CH$_3$O | CH |
| 3-CH$_3$ | H | CH$_3$ | CH$_3$O | CH$_3$O | CH |
| 6-CH$_3$ | H | CH$_3$ | CH$_3$O | CH$_3$O | CH |
| 6-(CH$_3$)$_2$CH | H | CH$_3$ | CH$_3$O | CH$_3$O | CH |
| 5-NO$_2$ | H | CH$_3$ | CH$_3$O | CH$_3$O | CH |
| 5-CH$_3$O | H | CH$_3$ | CH$_3$O | CH$_3$O | CH |
| 5-(CH$_3$)$_2$CHO | H | CH$_3$ | CH$_3$O | CH$_3$O | CH |
| 5-CF$_3$ | H | CH$_3$ | CH$_3$O | CH$_3$O | CH |
| 5-OCOCH$_3$ | H | CH$_3$ | CH$_3$O | CH$_3$O | CH |
| 3-CH$_3$ | 5-CH$_3$ | CH$_3$ | CH$_3$O | CH$_3$O | CH |
| 3-Cl | 5-CH$_3$ | CH$_3$ | CH$_3$O | CH$_3$O | CH |
| 5-F | H | CH$_3$ | CH$_3$ | CH$_3$ | N |
| 3-Cl | H | CH$_3$ | CH$_3$ | CH$_3$ | N |
| 4-Cl | H | CH$_3$ | CH$_3$ | CH$_3$ | N |
| 5-Cl | H | CH$_3$ | CH$_3$ | CH$_3$ | N |
| 6-Cl | H | CH$_3$ | CH$_3$ | CH$_3$ | N |
| 5-Br | H | CH$_3$ | CH$_3$ | CH$_3$ | N |
| 3-CH$_3$ | H | CH$_3$ | CH$_3$ | CH$_3$ | N |
| 6-CH$_3$ | H | CH$_3$ | CH$_3$ | CH$_3$ | N |
| 6-(CH$_3$)$_2$CH | H | CH$_3$ | CH$_3$ | CH$_3$ | N |
| 5-NO$_2$ | H | CH$_3$ | CH$_3$ | CH$_3$ | N |
| 5-CH$_3$O | H | CH$_3$ | CH$_3$ | CH$_3$ | N |
| 5-(CH$_3$)$_2$CHO | H | CH$_3$ | CH$_3$ | CH$_3$ | N |
| 5-CF$_3$ | H | CH$_3$ | CH$_3$ | CH$_3$ | N |
| 5-OCOCH$_3$ | H | CH$_3$ | CH$_3$ | CH$_3$ | N |
| 3-CH$_3$ | 5-CH$_3$ | CH$_3$ | CH$_3$ | CH$_3$ | N |
| 3-Cl | 5-CH$_3$ | CH$_3$ | CH$_3$ | CH$_3$ | N |
| 5-F | H | CH$_3$ | CH$_3$O | CH$_3$ | N |
| 3-Cl | H | CH$_3$ | CH$_3$O | CH$_3$ | N |
| 4-Cl | H | CH$_3$ | CH$_3$O | CH$_3$ | N |
| 5-Cl | H | CH$_3$ | CH$_3$O | CH$_3$ | N |
| 6-Cl | H | CH$_3$ | CH$_3$O | CH$_3$ | N |
| 5-Br | H | CH$_3$ | CH$_3$O | CH$_3$ | N |
| 3-CH$_3$ | H | CH$_3$ | CH$_3$O | CH$_3$ | N |
| 6-CH$_3$ | H | CH$_3$ | CH$_3$O | CH$_3$ | N |
| 6-(CH$_3$)$_2$CH | H | CH$_3$ | CH$_3$O | CH$_3$ | N |
| 5-NO$_2$ | H | CH$_3$ | CH$_3$O | CH$_3$ | N |
| 5-CH$_3$O | H | CH$_3$ | CH$_3$O | CH$_3$ | N |
| 5-(CH$_3$)$_2$CHO | H | CH$_3$ | CH$_3$O | CH$_3$ | N |
| 5-CF$_3$ | H | CH$_3$ | CH$_3$O | CH$_3$ | N |
| 5-OCOCH$_3$ | H | CH$_3$ | CH$_3$O | CH$_3$ | N |
| 3-CH$_3$ | 5-CH$_3$ | CH$_3$ | CH$_3$O | CH$_3$ | N |
| 3-Cl | 5-CH$_3$ | CH$_3$ | CH$_3$O | CH$_3$ | N |
| 5-F | H | CH$_3$ | CH$_3$O | CH$_3$O | N |
| 3-Cl | H | CH$_3$ | CH$_3$O | CH$_3$O | N |
| 4-Cl | H | CH$_3$ | CH$_3$O | CH$_3$O | N |
| 5-Cl | H | CH$_3$ | CH$_3$O | CH$_3$O | N |
| 6-Cl | H | CH$_3$ | CH$_3$O | CH$_3$O | N |
| 5-Br | H | CH$_3$ | CH$_3$O | CH$_3$O | N |
| 3-CH$_3$ | H | CH$_3$ | CH$_3$O | CH$_3$O | N |
| 6-CH$_3$ | H | CH$_3$ | CH$_3$O | CH$_3$O | N |
| 6-(CH$_3$)$_2$CH | H | CH$_3$ | CH$_3$O | CH$_3$O | N |
| 5-NO$_2$ | H | CH$_3$ | CH$_3$O | CH$_3$O | N |
| 5-CH$_3$O | H | CH$_3$ | CH$_3$O | CH$_3$O | N |
| 5-(CH$_3$)$_2$CHO | H | CH$_3$ | CH$_3$O | CH$_3$O | N |
| 5-CF$_3$ | H | CH$_3$ | CH$_3$O | CH$_3$O | N |
| 5-OCOCH$_3$ | H | CH$_3$ | CH$_3$O | CH$_3$O | N |
| 3-CH$_3$ | 5-CH$_3$ | CH$_3$ | CH$_3$O | CH$_3$O | N |
| 3-Cl | 5-CH$_3$ | CH$_3$ | CH$_3$O | CH$_3$O | N |
| H | H | CH$_3$ | H | CH$_3$ | CH |
| H | H | CH$_3$ | Cl | CH$_3$ | CH |

TABLE V-continued

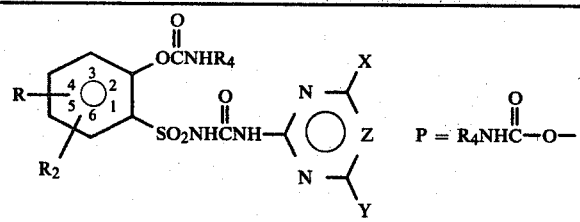

| R1 | R2 | R4 | X | Y | Z |
|---|---|---|---|---|---|
| H | H | CH3 | Br | CH3 | CH |
| H | H | CH3 | C2H5 | CH3 | CH |
| H | H | CH3 | CH3(CH2)2O | CH3 | CH |
| H | H | CH3 | CF3 | CH3 | CH |
| H | H | CH3 | CH3S | CH3 | CH |
| H | H | CH3 | CH3OCH2 | CH3 | CH |
| 3-Cl | 5-Cl | CH3 | H | CH3 | CH |
| 3-Cl | 5-Cl | CH3 | Cl | CH3 | CH |
| 3-Cl | 5-Cl | CH3 | Br | CH3 | CH |
| 3-Cl | 5-Cl | CH3 | C2H5 | CH3 | CH |
| 3-Cl | 5-Cl | CH3 | CH3(CH2)2O | CH3 | CH |
| 3-Cl | 5-Cl | CH3 | CF3 | CH3 | CH |
| 3-Cl | 5-Cl | CH3 | CH3S | CH3 | CH |
| 3-Cl | 5-Cl | CH3 | CH3OCH2 | CH3 | CH |
| H | H | CH3 | CH3 | CH3 | CCl |
| H | H | CH3 | CH3 | CH3 | CBr |
| H | H | CH3 | CH3 | CH3 | CCN |
| H | H | CH3 | CH3 | CH3 | CCH3 |
| H | H | CH3 | CH3 | CH3 | CC2H5 |
| H | H | CH3 | CH3 | CH3 | CCH2CH2Cl |
| H | H | CH3 | CH3 | CH3 | CCH2CH=CH2 |
| 3-Cl | 5-Cl | CH3 | CH3 | CH3 | CCl |
| 3-Cl | 5-Cl | CH3 | CH3 | CH3 | CBr |
| 3-Cl | 5-Cl | CH3 | CH3 | CH3 | CCN |
| 3-Cl | 5-Cl | CH3 | CH3 | CH3 | CCH3 |
| 3-Cl | 5-Cl | CH3 | CH3 | CH3 | CC2H5 |
| 3-Cl | 5-Cl | CH3 | CH3 | CH3 | CCH2CH2Cl |
| 3-Cl | 5-Cl | CH3 | CH3 | CH3 | CCH2CH=CH2 |

TABLE VI

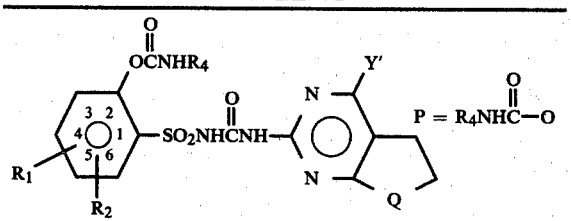

| R1 | R2 | R4 | Y' | Q |
|---|---|---|---|---|
| 3-Cl | 5-Cl | CH3 | H | O |
| 3-Cl | 5-Cl | CH3 | CH3 | O |
| 3-Cl | 5-Cl | CH3 | OCH3 | O |
| 3-Cl | 5-Cl | CH3 | Cl | O |
| 3-Cl | 5-Cl | CH3 | H | CH2 |
| 3-Cl | 5-Cl | CH3 | CH3 | CH2 |
| 3-Cl | 5-Cl | CH3 | OCH3 | CH2 |
| 3-Cl | 5-Cl | CH3 | Cl | CH2 |
| H | H | CH3 | H | O |

TABLE VI-continued

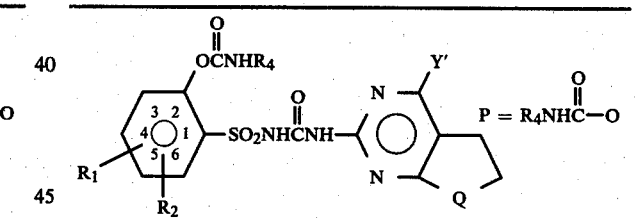

| R1 | R2 | R4 | Y' | Q |
|---|---|---|---|---|
| H | H | CH3 | CH3 | O |
| H | H | CH3 | OCH3 | O |
| H | H | CH3 | Cl | O |
| H | H | CH3 | H | CH2 |
| H | H | CH3 | CH3 | CH2 |
| H | H | CH3 | OCH3 | CH2 |
| H | H | CH3 | Cl | CH2 |

TABLE VII

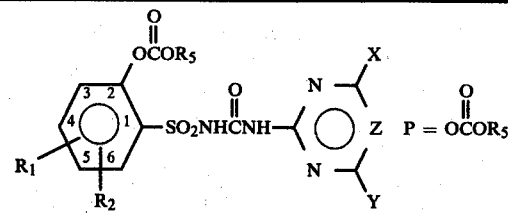

| R1 | R2 | R5 | X | Y | Z |
|---|---|---|---|---|---|
| H | H | CH3 | CH3 | CH3 | CH |
| H | H | CH3(CH2)4 | CH3 | CH3 | CH |

TABLE VII-continued

Structure:
- Benzene ring with positions 1-6, bearing OCOR5 ester group (OC(O)OR5) at position 2, SO2NHCNH-C(O)- at position 1, R1 at position 5, R2 at position 6
- Connected via urea linkage to a 6-membered heterocycle with N at two positions, X and Y on adjacent carbons, Z in the ring
- P = OCOR5

| R₁ | R₂ | R₅ | X | Y | Z |
|---|---|---|---|---|---|
| H | H | phenyl | CH₃ | CH₃ | CH |
| H | H | 4-methylphenyl | CH₃ | CH₃ | CH |
| H | H | 4-chlorophenyl | CH₃ | CH₃ | CH |
| H | H | 3-chlorophenyl | CH₃ | CH₃ | CH |
| H | H | 2-chlorophenyl | CH₃ | CH₃ | CH |
| H | H | CH₃ | CH₃O | CH₃ | CH |
| H | H | CH₃(CH₂)₄ | CH₃O | CH₃ | CH |
| H | H | phenyl | CH₃O | CH₃ | CH |
| H | H | 4-methylphenyl | CH₃O | CH₃ | CH |
| H | H | 4-chlorophenyl | CH₃O | CH₃ | CH |
| H | H | 3-chlorophenyl | CH₃O | CH₃ | CH |
| H | H | 2-chlorophenyl | CH₃O | CH₃ | CH |
| H | H | CH₃ | CH₃O | CH₃ | N |
| H | H | CH₃(CH₂)₄ | CH₃O | CH₃ | N |
| H | H | phenyl | CH₃O | CH₃ | N |
| H | H | 4-methylphenyl | CH₃O | CH₃ | N |
| H | H | 4-chlorophenyl | CH₃O | CH₃ | N |
| H | H | 3-chlorophenyl | CH₃O | CH₃ | N |

TABLE VII-continued

Structure: Aryl ring with OCOR5 (via O-C(=O)) at position 2, SO2NHCNH-C(...)- at position 1, R1 at position 4, R2 at position 5; connected to a heterocyclic ring with X, Y, Z substituents. P = OCOR5.

| R₁ | R₂ | R₅ | X | Y | Z |
|---|---|---|---|---|---|
| H | H | 2-Cl-phenyl | CH₃O | CH₃ | N |
| H | H | CH₃ | CH₃O | CH₃O | N |
| H | H | CH₃(CH₂)₄ | CH₃O | CH₃O | N |
| H | H | phenyl | CH₃O | CH₃O | N |
| H | H | 4-CH₃-phenyl | CH₃O | CH₃O | N |
| H | H | 4-Cl-phenyl | CH₃O | CH₃O | N |
| H | H | 2-Cl-phenyl | CH₃O | CH₃O | N |
| H | H | 2-Cl-phenyl | CH₃O | CH₃O | N |
| 3-Cl | 5-Cl | CH₃ | CH₃ | CH₃ | CH |
| 3-Cl | 5-Cl | CH₃(CH₂)₄ | CH₃ | CH₃ | CH |
| 3-Cl | 5-Cl | phenyl | CH₃ | CH₃ | CH |
| 3-Cl | 5-Cl | 4-CH₃-phenyl | CH₃ | CH₃ | CH |
| 3-Cl | 5-Cl | 4-Cl-phenyl | CH₃ | CH₃ | CH |
| 3-Cl | 5-Cl | 2-Cl-phenyl | CH₃ | CH₃ | CH |
| 3-Cl | 5-Cl | 2-Cl-phenyl | CH₃ | CH₃ | CH |
| 3-Cl | 5-Cl | CH₃ | CH₃O | CH₃ | CH |
| 3-Cl | 5-Cl | CH₃(CH₂)₄ | CH₃O | CH₃ | CH |
| 3-Cl | 5-Cl | phenyl | CH₃O | CH₃ | CH |
| 3-Cl | 5-Cl | 4-CH₃-phenyl | CH₃O | CH₃ | CH |
| 3-Cl | 5-Cl | 4-Cl-phenyl | CH₃O | CH₃ | CH |

TABLE VII-continued $$\underset{R_1}{\overset{OCOR_5}{\underset{R_2}{\text{phenyl}}}}-SO_2NHCNH-\underset{N}{\overset{N}{\underset{Y}{\text{het}}}} \quad P = OCOR_5$$

| R₁ | R₂ | R₅ | X | Y | Z |
|---|---|---|---|---|---|
| 3-Cl | 5-Cl | 3-Cl-phenyl | CH₃O | CH₃ | CH |
| 3-Cl | 5-Cl | 2-Cl-phenyl | CH₃O | CH₃ | CH |
| 3-Cl | 5-Cl | CH₃ | CH₃O | CH₃O | CH |
| 3-Cl | 5-Cl | CH₃(CH₂)₄ | CH₃O | CH₃O | CH |
| 3-Cl | 5-Cl | phenyl | CH₃O | CH₃O | CH |
| 3-Cl | 5-Cl | 4-CH₃-phenyl | CH₃O | CH₃O | CH |
| 3-Cl | 5-Cl | 4-Cl-phenyl | CH₃O | CH₃O | CH |
| 3-Cl | 5-Cl | 3-Cl-phenyl | CH₃O | CH₃O | CH |
| 3-Cl | 5-Cl | 2-Cl-phenyl | CH₃O | CH₃O | CH |
| 3-Cl | 5-Cl | CH₃ | CH₃ | CH₃ | N |
| 3-Cl | 5-Cl | CH₃(CH₂)₄ | CH₃ | CH₃ | N |
| 3-Cl | 5-Cl | phenyl | CH₃ | CH₃ | N |
| 3-Cl | 5-Cl | 4-CH₃-phenyl | CH₃ | CH₃ | N |
| 3-Cl | 5-Cl | 4-Cl-phenyl | CH₃ | CH₃ | N |
| 3-Cl | 5-Cl | 3-Cl-phenyl | CH₃ | CH₃ | N |
| 3-Cl | 5-Cl | 2-Cl-phenyl | CH₃ | CH₃ | N |
| 3-Cl | 5-Cl | CH₃ | CH₃O | CH₃ | N |
| 3-Cl | 5-Cl | CH₃(CH₂)₄ | CH₃O | CH₃ | N |
| 3-Cl | 5-Cl | phenyl | CH₃O | CH₃ | N |

TABLE VII-continued

Structure: benzene ring with OCOR5 (ester at position 2), SO2NHCNH-- linking to pyrimidine ring with substituents X, Y, Z; R1 at position 4/5, R2 at position 5/6; P = OCOR5

| R1 | R2 | R5 | X | Y | Z |
|---|---|---|---|---|---|
| 3-Cl | 5-Cl | CH3—⌬— (4-methylphenyl) | CH3O | CH3 | N |
| 3-Cl | 5-Cl | Cl—⌬— (4-chlorophenyl) | CH3O | CH3 | N |
| 3-Cl | 5-Cl | 3-chlorophenyl | CH3O | CH3 | N |
| 3-Cl | 5-Cl | 2-chlorophenyl | CH3O | CH3 | N |
| 3-Cl | 5-Cl | CH3 | CH3O | CH3O | N |
| 3-Cl | 5-Cl | CH3(CH2)4 | CH3O | CH3O | N |
| 3-Cl | 5-Cl | phenyl | CH3O | CH3O | N |
| 3-Cl | 5-Cl | CH3—⌬— (4-methylphenyl) | CH3O | CH3O | N |
| 3-Cl | 5-Cl | Cl—⌬— (4-chlorophenyl) | CH3O | CH3O | N |
| 3-Cl | 5-Cl | 3-chlorophenyl | CH3O | CH3O | N |
| 3-Cl | 5-Cl | 2-chlorophenyl | CH3O | CH3O | N |
| 5-F | H | CH3 | CH3 | CH3 | CH |
| 3-Cl | H | CH3 | CH3 | CH3 | CH |
| 4-Cl | H | CH3 | CH3 | CH3 | CH |
| 5-Cl | H | CH3 | CH3 | CH3 | CH |
| 6-Cl | H | CH3 | CH3 | CH3 | CH |
| 5-Br | H | CH3 | CH3 | CH3 | CH |
| 3-CH3 | H | CH3 | CH3 | CH3 | CH |
| 6-CH3 | H | CH3 | CH3 | CH3 | CH |
| 6-(CH3)2CH | H | CH3 | CH3 | CH3 | CH |
| 5-NO2 | H | CH3 | CH3 | CH3 | CH |
| 5-CH3O | H | CH3 | CH3 | CH3 | CH |
| 5-(CH3)2CHO | H | CH3 | CH3 | CH3 | CH |
| 5-CF3 | H | CH3 | CH3 | CH3 | CH |
| 5-OCOCH3 | H | CH3 | CH3 | CH3 | CH |
| 3-CH3 | 5-CH3 | CH3 | CH3 | CH3 | CH |
| 3-Cl | 5-CH3 | CH3 | CH3 | CH3 | CCl |
| H | H | CH3 | CH3 | CH3 | CBr |
| H | H | CH3 | CH3 | CH3 | CCN |
| H | H | CH3 | CH3 | CH3 | CCH3 |
| H | H | CH3 | CH3 | CH3 | CC2H5 |
| H | H | CH3 | CH3 | CH3 | CCH2CH2Cl |
| H | H | CH3 | CH3 | CH3 | CCH2CH=CH2 |
| 3-Cl | 5-Cl | CH3 | CH3 | CH3 | CCl |
| 3-Cl | 5-Cl | CH3 | CH3 | CH3 | CBr |
| 3-Cl | 5-Cl | CH3 | CH3 | CH3 | CCN |
| 3-Cl | 5-Cl | CH3 | CH3 | CH3 | CCH3 |

TABLE VII-continued

[Structure: phenyl ring with OCOR5 (ortho position marked 2), positions labeled 1-6 with R1 at 5 and R2 at 6, SO2NHCNH-(C=O)- linked to a ring with N, X, Y, Z substituents. P = OCOR5]

| R1 | R2 | R5 | X | Y | Z |
|---|---|---|---|---|---|
| 3-Cl | 5-Cl | CH3 | CH3 | CH3 | CC2H5 |
| 3-Cl | 5-Cl | CH3 | CH3 | CH3 | CCH2CH2Cl |
| 3-Cl | 5-Cl | CH3 | CH3 | CH3 | CCH2CH=CH2 |
| H | H | CH3 | CH3O | CH3O | CH |
| H | H | CH3(CH2)4 | CH3O | CH3O | CH |
| H | H | C6H5 (phenyl) | CH3O | CH3O | CH |
| H | H | 4-CH3-C6H4 | CH3O | CH3O | CH |
| H | H | 4-Cl-C6H4 | CH3O | CH3O | CH |
| H | H | 3-Cl-C6H4 | CH3O | CH3O | CH |
| H | H | 2-Cl-C6H4 | CH3O | CH3O | CH |
| H | H | CH3 | CH3 | CH3 | N |
| H | H | CH3(CH2)4 | CH3 | CH3 | N |
| H | H | C6H5 (phenyl) | CH3 | CH3 | N |
| H | H | 4-CH3-C6H4 | CH3 | CH3 | N |
| H | H | 4-Cl-C6H4 | CH3 | CH3 | N |
| H | H | 3-Cl-C6H4 | CH3 | CH3 | N |
| H | H | 2-Cl-C6H4 | CH3 | CH3 | N |
| 5-F | H | CH3 | CH3O | CH3 | CH |
| 3-Cl | H | CH3 | CH3O | CH3 | CH |
| 4-Cl | H | CH3 | CH3O | CH3 | CH |
| 5-Cl | H | CH3 | CH3O | CH3 | CH |
| 6-Cl | H | CH3 | CH3O | CH3 | CH |
| 5-Br | H | CH3 | CH3O | CH3 | CH |
| 3-CH3 | H | CH3 | CH3O | CH3 | CH |
| 6-CH3 | H | CH3 | CH3O | CH3 | CH |
| 6-(CH3)2CH | H | CH3 | CH3O | CH3 | CH |
| 5-NO2 | H | CH3 | CH3O | CH3 | CH |
| 5-CH3O | H | CH3 | CH3O | CH3 | CH |
| 5-(CH3)2CHO | H | CH3 | CH3O | CH3 | CH |
| 5-CF3 | H | CH3 | CH3O | CH3 | CH |
| 5-OCOCH3 | H | CH3 | CH3O | CH3 | CH |
| 3-CH3 | 5-CH3 | CH3 | CH3O | CH3 | CH |
| 3-Cl | 5-CH3 | CH3 | CH3O | CH3 | CH |

TABLE VII-continued

Structure: 2-OCOR$_5$ substituted benzene with SO$_2$NHCNH-pyrimidine/triazine; P = OCOR$_5$

| R$_1$ | R$_2$ | R$_5$ | X | Y | Z |
|---|---|---|---|---|---|
| 5-F | H | CH$_3$ | CH$_3$O | CH$_3$O | CH |
| 3-Cl | H | CH$_3$ | CH$_3$O | CH$_3$O | CH |
| 4-Cl | H | CH$_3$ | CH$_3$O | CH$_3$O | CH |
| 5-Cl | H | CH$_3$ | CH$_3$O | CH$_3$O | CH |
| 6-Cl | H | CH$_3$ | CH$_3$O | CH$_3$O | CH |
| 5-Br | H | CH$_3$ | CH$_3$O | CH$_3$O | CH |
| 3-CH$_3$ | H | CH$_3$ | CH$_3$O | CH$_3$O | CH |
| 6-CH$_3$ | H | CH$_3$ | CH$_3$O | CH$_3$O | CH |
| 6-(CH$_3$)$_2$CH | H | CH$_3$ | CH$_3$O | CH$_3$O | CH |
| 5-NO$_2$ | H | CH$_3$ | CH$_3$O | CH$_3$O | CH |
| 5-CH$_3$O | H | CH$_3$ | CH$_3$O | CH$_3$O | CH |
| 5-(CH$_3$)$_2$CHO | H | CH$_3$ | CH$_3$O | CH$_3$O | CH |
| 5-CF$_3$ | H | CH$_3$ | CH$_3$O | CH$_3$O | CH |
| 5-OCOCH$_3$ | H | CH$_3$ | CH$_3$O | CH$_3$O | CH |
| 3-CH$_3$ | 5-CH$_3$ | CH$_3$ | CH$_3$O | CH$_3$O | CH |
| 3-Cl | 5-CH$_3$ | CH$_3$ | CH$_3$O | CH$_3$O | CH |
| 5-F | H | CH$_3$ | CH$_3$ | CH$_3$ | N |
| 3-Cl | H | CH$_3$ | CH$_3$ | CH$_3$ | N |
| 4-Cl | H | CH$_3$ | CH$_3$ | CH$_3$ | N |
| 5-Cl | H | CH$_3$ | CH$_3$ | CH$_3$ | N |
| 6-Cl | H | CH$_3$ | CH$_3$ | CH$_3$ | N |
| 5-Br | H | CH$_3$ | CH$_3$ | CH$_3$ | N |
| 3-CH$_3$ | H | CH$_3$ | CH$_3$ | CH$_3$ | N |
| 6-CH$_3$ | H | CH$_3$ | CH$_3$ | CH$_3$ | N |
| 6-(CH$_3$)$_2$CH | H | CH$_3$ | CH$_3$ | CH$_3$ | N |
| 5-NO$_2$ | H | CH$_3$ | CH$_3$ | CH$_3$ | N |
| 5-CH$_3$O | H | CH$_3$ | CH$_3$ | CH$_3$ | N |
| 5-(CH$_3$)$_2$CHO | H | CH$_3$ | CH$_3$ | CH$_3$ | N |
| 5-CF$_3$ | H | CH$_3$ | CH$_3$ | CH$_3$ | N |
| 5-OCOCH$_3$ | H | CH$_3$ | CH$_3$ | CH$_3$ | N |
| 3-CH$_3$ | 5-CH$_3$ | CH$_3$ | CH$_3$ | CH$_3$ | N |
| 3-Cl | 5-CH$_3$ | CH$_3$ | CH$_3$ | CH$_3$ | N |
| 5-F | H | CH$_3$ | CH$_3$O | CH$_3$ | N |
| 3-Cl | H | CH$_3$ | CH$_3$O | CH$_3$ | N |
| 4-Cl | H | CH$_3$ | CH$_3$O | CH$_3$ | N |
| 5-Cl | H | CH$_3$ | CH$_3$O | CH$_3$ | N |
| 6-Cl | H | CH$_3$ | CH$_3$O | CH$_3$ | N |
| 5-Br | H | CH$_3$ | CH$_3$O | CH$_3$ | N |
| 3-CH$_3$ | H | CH$_3$ | CH$_3$O | CH$_3$ | N |
| 6-CH$_3$ | H | CH$_3$ | CH$_3$O | CH$_3$ | N |
| 6-(CH$_3$)$_2$CH | H | CH$_3$ | CH$_3$O | CH$_3$ | N |
| 5-NO$_2$ | H | CH$_3$ | CH$_3$O | CH$_3$ | N |
| 5-CH$_3$O | H | CH$_3$ | CH$_3$O | CH$_3$ | N |
| 5-(CH$_3$)$_2$CHO | H | CH$_3$ | CH$_3$O | CH$_3$ | N |
| 5-CF$_3$ | H | CH$_3$ | CH$_3$O | CH$_3$ | N |
| 5-OCOCH$_3$ | H | CH$_3$ | CH$_3$O | CH$_3$ | N |
| 3-CH$_3$ | 5-CH$_3$ | CH$_3$ | CH$_3$O | CH$_3$ | N |
| 3-Cl | 5-CH$_3$ | CH$_3$ | CH$_3$O | CH$_3$ | N |
| 5-F | H | CH$_3$ | CH$_3$O | CH$_3$O | N |
| 3-Cl | H | CH$_3$ | CH$_3$O | CH$_3$O | N |
| 4-Cl | H | CH$_3$ | CH$_3$O | CH$_3$O | N |
| 5-Cl | H | CH$_3$ | CH$_3$O | CH$_3$O | N |
| 6-Cl | H | CH$_3$ | CH$_3$O | CH$_3$O | N |
| 5-Br | H | CH$_3$ | CH$_3$O | CH$_3$O | N |
| 3-CH$_3$ | H | CH$_3$ | CH$_3$O | CH$_3$O | N |
| 6-CH$_3$ | H | CH$_3$ | CH$_3$O | CH$_3$O | N |
| 6-(CH$_3$)$_2$CH | H | CH$_3$ | CH$_3$O | CH$_3$O | N |
| 5-NO$_2$ | H | CH$_3$ | CH$_3$O | CH$_3$O | N |
| 5-CH$_3$O | H | CH$_3$ | CH$_3$O | CH$_3$O | N |
| 5-(CH$_3$)$_2$CHO | H | CH$_3$ | CH$_3$O | CH$_3$O | N |
| 5-CF$_3$ | H | CH$_3$ | CH$_3$O | CH$_3$O | N |
| 5-OCOCH$_3$ | H | CH$_3$ | CH$_3$O | CH$_3$O | N |
| 3-CH$_3$ | 5-CH$_3$ | CH$_3$ | CH$_3$O | CH$_3$O | N |
| 3-Cl | 5-CH$_3$ | CH$_3$ | CH$_3$O | CH$_3$O | N |
| H | H | CH$_3$ | H | CH$_3$ | CH |
| H | H | CH$_3$ | Cl | CH$_3$ | CH |
| H | H | CH$_3$ | Br | CH$_3$ | CH |
| H | H | CH$_3$ | C$_2$H$_5$ | CH$_3$ | CH |
| H | H | CH$_3$ | CH$_3$(CH$_2$)$_2$O | CH$_3$ | CH |
| H | H | CH$_3$ | CF$_3$ | CH$_3$ | CH |

TABLE VII-continued

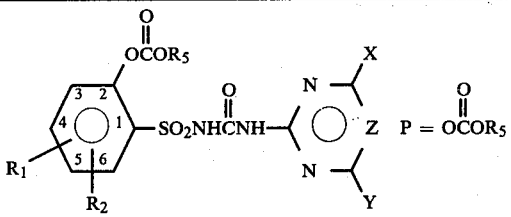

| R₁ | R₂ | R₅ | X | Y | Z |
|---|---|---|---|---|---|
| H | H | $CH_3$ | $CH_3S$ | $CH_3$ | CH |
| H | H | $CH_3$ | $CH_3OCH_2$ | $CH_3$ | CH |
| 3-Cl | 5-Cl | $CH_3$ | H | $CH_3$ | CH |
| 3-Cl | 5-Cl | $CH_3$ | Cl | $CH_3$ | CH |
| 3-Cl | 5-Cl | $CH_3$ | Br | $CH_3$ | CH |
| 3-Cl | 5-Cl | $CH_3$ | $C_2H_5$ | $CH_3$ | CH |
| 3-Cl | 5-Cl | $CH_3$ | $CH_3(CH_2)_2O$ | $CH_3$ | CH |
| 3-Cl | 5-Cl | $CH_3$ | $CF_3$ | $CH_3$ | CH |
| 3-Cl | 5-Cl | $CH_3$ | $CH_3S$ | $CH_3$ | CH |
| 3-Cl | 5-Cl | $CH_3$ | $CH_3OCH_2$ | $CH_3$ | CH |

TABLE VIII

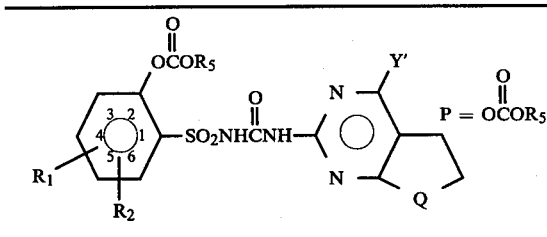

| R₁ | R₂ | R₅ | Y' | Q |
|---|---|---|---|---|
| 3-Cl | 5-Cl | $CH_3$ | H | O |
| 3-Cl | 5-Cl | $CH_3$ | $CH_3$ | O |
| 3-Cl | 5-Cl | $CH_3$ | $OCH_3$ | O |
| 3-Cl | 5-Cl | $CH_3$ | Cl | O |
| 3-Cl | 5-Cl | $CH_3$ | H | $CH_2$ |
| 3-Cl | 5-Cl | $CH_3$ | $CH_3$ | $CH_2$ |
| 3-Cl | 5-Cl | $CH_3$ | $OCH_3$ | $CH_2$ |
| 3-Cl | 5-Cl | $CH_3$ | Cl | $CH_2$ |
| H | H | $CH_3$ | H | O |
| H | H | $CH_3$ | $CH_3$ | O |
| H | H | $CH_3$ | $OCH_3$ | O |
| H | H | $CH_3$ | Cl | O |
| H | H | $CH_3$ | H | $CH_2$ |
| H | H | $CH_3$ | $CH_3$ | $CH_2$ |
| H | H | $CH_3$ | $OCH_3$ | $CH_2$ |
| H | H | $CH_3$ | Cl | $CH_2$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IX

| | Active* Ingredient | Diluent(s) | Surfactant(s) |
|---|---|---|---|
| Wettable Powders | 20-90 | 0-74 | 1-10 |
| Oil Suspensions, Emulsions, Solutions (including Emulsifiable Concentrates | 3-50 | 40-95 | 0-15 |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |
| High-Strength Compositions | 90-99 | 0-10 | 0-2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 1, line 62 and Examples 8, 12, 15, 39, 41, 52, 53, 58, 132, 138-140, 162-164, 166, 167 and 169-182.

H. Gysin and E. Knusli, U.S. Pat. No. 2,891,855, June 23, 1959, Col. 5, line 66 through Col. 5, line 17 and Examples 1-4.

G. C. Klingman, "Weed Control as a Science", John Wiley & Sons, Inc., New York, 1961, pp. 81-96.

J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 3

Wettable Powder

| | |
|---|---|
| 3,5-dichloro-N—[(4,6-dimethoxypyrimidin-2-yl)aminocarbonyl]-2-hydroxybenzenesulfonamide, acetate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until the solids are substantially under 50 microns and then reblended.

EXAMPLE 4

Wettable Powder

| | |
|---|---|
| 3,5-dichloro-N—[(4,6-dimethypyrimidin-2-yl)aminocarbonyl]-2-hydroxybenzenesulfonamide, acetate | 50% |
| sodium alkylnaphthalenesulfonate | 2% |
| low-viscosity methyl cellulose | 2% |
| diatomaceous earth | 46% |

The ingredients are blended, coarsely hammer-milled and then air-milled to produce particles of active substantially all below 10 microns in diameter. The product is reblended before packaging.

EXAMPLE 5

Granule

| | |
|---|---|
| wettable powder of Example 4 | 5% |
| attapulgite granules (U.S.S. 20-40 mesh; 0.84-0.42 mm) | 95% |

A slurry of wettable powder containing ≈25% solids is sprayed on the surface of attapulgite granules in a double-cone blender. The granules are dried and packaged.

EXAMPLE 6

Extruded Pellet

| | |
|---|---|
| 3,5-dichloro-2-hydroxy-N—[(4-methoxy-6-methyl-pyrimidin-2-yl)aminocarbonyl]-benzenesulfonamide, acetate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

Oil Suspension

| | |
|---|---|
| 3,5-dichloro-N—[(4,6-dimethoxypyrimidin-2-yl)aminocarbonyl]-2-hydroxybenzenesulfaonamide, acetate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 8

Wettable Powder

| | |
|---|---|
| 3,5-dichloro-2-hydroxy-N—[(4-methoxy-6-methyl-pyrimidin-2-yl)aminocarbonyl]benzenesulfonamide, acetate | 20% |
| sodium alkylnaphthalenesulfonate | 4% |
| sodium ligninsulfonate | 4% |
| low-viscosity methyl cellulose | 3% |
| attapulgite | 69% |

The ingredients are thoroughly blended. After grinding in a hammer-mill to produce particles substantially all below 100 microns, the material is reblended and sifted through a U.S.S. No. 50 sieve (0.3 mm opening) and packaged.

EXAMPLE 9

Low-Strength Granule

| | |
|---|---|
| 3,5-dichloro-2-hydroxy-N—[(4-methoxy-6-methyl-pyrimidin-2-yl)aminocarbonyl]benzenesulfonamide, acetate | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension

| | |
|---|---|
| 3,5-dichloro-N—[(4,6-dimethylpyrimidin-2-yl)aminocarbonyl]-2-hydroxybenzenesulfonamide, acetate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles substantially all under 5 microns in size.

EXAMPLE 11

Solution

| | |
|---|---|
| 3,5-dichloro-2-hydroxy-N—[(4-methoxy-6-methyl-pyrimidin-2-yl)aminocarbonyl]benzenesulfonamide, acetate sodium salt | 5% |
| water | 95% |

The salt is added directly to the water with stirring to produce the solution, which may then be packaged for use.

EXAMPLE 12

Low-Strength Granule

| | |
|---|---|
| 3,5-dichloro-N—[(4,6-dimethoxypyrimidin-2-yl)aminocarbonyl]-2-hydroxybenzenesulfonamide, acetate | 0.1% |
| attapulgite granules (U.S.S. 20–40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 13

Granule

| | |
|---|---|
| 3,5-dichloro-2-hydroxy-N—[(4-methoxy-6-methyl-pyrimidin-2-yl)aminocarbonyl]benzenesulfonamide, acetate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 14

High-Strength Concentrate

| | |
|---|---|
| 3,5-dichloro-N—[(4,6-dimethoxypyrimidin-2-yl)aminocarbonyl]-2-hydroxybenzenesulfonamide, acetate | 99% |
| silica aerogel | 0.5% |
| synthetic amorphous silica | 0.5% |

The ingredients are blended and ground in a hammer-mill to produce a material substantially all passing a U.S.S. No. 50 screen (0.3 mm opening). The concentrate may be formulated further if necessary.

EXAMPLE 15

Wettable Powder

| | |
|---|---|
| 3,5-dichloro-N—[(4,6-dimethylpyrimidin-2-yl)aminocarbonyl]-2-hydroxybenzenesulfonamide, acetate | 90.0% |
| dioctyl sodium sulfosuccinate | 0.1% |
| synthetic fine silica | 9.9% |

The ingredients are blended and ground in a hammer-mill to produce particles substantially all below 100 microns. The material is sifted through a U.S.S. No. 50 screen and then packaged.

EXAMPLE 16

Wettable Powder

| | |
|---|---|
| 3,5-dichloro-2-hydroxy-N—[(4-methoxy-6-methyl-pyrimidin-2-yl)aminocarbonyl]benzenesulfonamide, acetate | 40% |
| sodium ligninsulfonate | 20% |
| montmorillonite clay | 40% |

The ingredients are thoroughly blended, coarsely hammer-milled and then air-milled to produce particles substantially all below 10 microns in size. The material is reblended and then packaged.

EXAMPLE 17

Dust

| | |
|---|---|
| 3,5-dichloro-N—[(4,6-dimethoxypyrimidin-2-yl)aminocarbonyl]-2-hydroxybenzenesulfonamide, acetate | 10% |
| attapulgite | 10% |
| pyrophyllite | 80% |

The active ingredient is blended with attapulgite and then passed through a hammer mill to produce particles substantially all below 200 microns. The ground concentrate is then blended with powdered pyrophyllite until homogeneous.

Utility

The compounds of the present invention are active herbicides. They have utility for broad spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate and time of application, compounds of this invention may be used to modify plant growth beneficially, and also selectively control weeds in crops such as wheat, rice, corn, and various leguminous crops.

The precise amount of the compound of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethylurea (diuron); the triazines such as 2-chloro-4-(ethylamino)-6-(isopropylamino)-s-triazine (atrazine); the uracils such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamide); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl)diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); 2-chloro-2',6'-diethyl(methoxymethyl)acetanilide (alachlor); 1,1-dimethyl-3-(α,α,α-trifluoro-m-tolyl)urea (fluometuron), S-(4-chlorobenzyl)N,N-diethylthiolcarbamate (benthiocarb); and N-(butoxymethyl)-2-chloro-2',6'-diethylacetanilide (butachlor).

The activity of these compounds was discovered in greenhouse tests. The tests are described and the data resulting from them are shown below.

TEST PROCEDURE

Seeds of crabgrass (Digitaria sp.), barnyardgrass (Echinochloa crusgalli), wild oats (Avena fatua, Cassia tora, morningglory (Ipomoea sp.), cocklebur (Xanthium sp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), sorghum with three leaves, corn with three leaves, soybean with two cotyledonary leaves, rice with two leaves, wheat with one leaf, and nutsedge with three-fives leaves were sprayed. Treated plants and controls were maintained in a greenhouse for 16 days, then all species were compared to controls and visually rated for response to treatment.

Ratings for compounds tested by this procedure are recorded in Table A.
0=no effect
& or 10=maximum effect
B=burn
C=chlorosis or necrosis
G=growth retardation
H=formative effects

TABLE A

| | kg/ha | |
|---|---|---|
| | 2/5 | 2/5 |
| POST-EMERGENCE | | |
| BUSHBEAN | 1C,1H | 1C,1H |
| COTTON | 2C,9G | 2B,4H,9G |
| MORNINGGLORY | 5H | 5H |
| COCKLEBUR | 8H | 5G |
| CASSIA | 2H | 4G |
| NUTSEDGE | 0 | 0 |
| CRABGRASS | 1B | 0 |
| BARNYARDGRASS | 1B | 0 |
| WILD OATS | 0 | 0 |
| WHEAT | 0 | 0 |
| CORN | 1C,5H | 0 |
| SOYBEAN | 1H,4G | 3H |
| RICE | 0 | 2G |
| SORGHUM | 3G | 4H |
| PRE-EMERGENCE | | |
| MORNINGGLORY | 8H | 5G |

TABLE A-continued

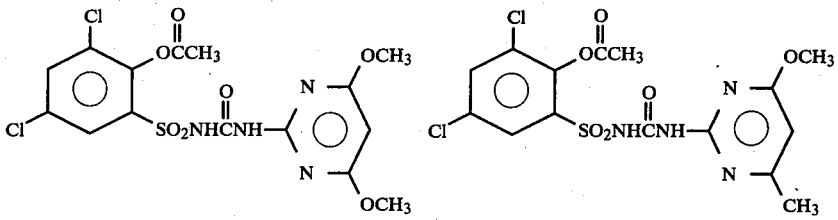

| | kg/ha | |
|---|---|---|
| | 2/5 | 2/5 |
| COCKLEBUR | 8H | 8G |
| CASSIA | 7G | 7G |
| NUTSEDGE | 5G | 0 |
| CRABGRASS | 0 | 0 |
| BARNYARDGRASS | 2C,5G | 0 |
| WILD OATS | 2G | 0 |
| WHEAT | 0 | 0 |
| CORN | 2G | 2G |
| SOYBEAN | 0 | 2G |
| RICE | 7H | 2G |
| SORGHUM | 2G | 4G |

What is claimed is:

1. A compound selected from:

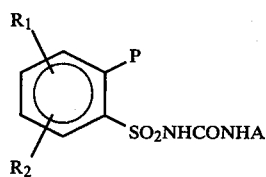 I wherein
P is

$R_1$ is H, F, Cl, Br, $C_1$-$C_3$ alkyl, $NO_2$, $C_1$-$C_3$ alkoxy, $CF_3$ or

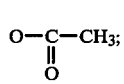

$R_2$ is H, $CH_3$ or Cl;
$R_3$ is H; $C_1$-$C_5$ alkyl; $C_2$-$C_3$ alkenyl; $C_2$-$C_3$ alkynyl; $C_1$-$C_4$ alkyl substituted with 1-3 substituents selected from 0-3 F, 0-3 Cl, 0-3 Br, and $OCH_3$; $C_2$-$C_3$ alkenyl substitutd with Cl; $C_3$-$C_6$ cycloalkyl; or

$R_4$ is $C_1$-$C_6$ alkyl; $C_3$-$C_4$ alkenyl; $C_3$-$C_6$ cycloalkyl; $C_5$-$C_6$ cycloalkyl substituted with $CH_3$;

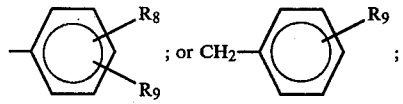

$R_5$ is $C_1$-$C_6$ alkyl or

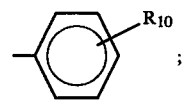

$R_6$ and $R_7$ are independently H, $NO_2$, $CH_3$, Cl or $OCH_3$;
$R_8$ is H, F, Cl, Br, $C_1$-$C_3$ alkyl, $NO_2$, CN, $SO_2CH_3$, $OCH_3$, $SCH_3$ or $CF_3$;
$R_9$ is H or $C_1$-$C_3$ alkyl;
$R_{10}$ is H, $CH_3$ or Cl;
A is

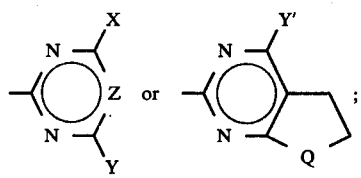

X is H, Cl, Br, $CH_3$, $CH_3CH_2$, $C_1$-$C_3$ alkoxy, $CF_3$, $CH_3S$ or $CH_3OCH_2$;
Y is $CH_3$ or $CH_3O$;
Z is N, CH, C—Cl, C—Br, C—CN, C—$CH_3$, —C—$CH_2CH_3$, C—$CH_2CH_2Cl$ or C—$CH_2CH$=$CH_2$;
Y' is H, $CH_3$, $OCH_3$ or Cl; and
Q is O or $CH_2$;
and their agriculturally suitable salts.

2. A compound of claim 1 wherein Z is N, CH, C—Cl, C—CN, C—Br or C—$CH_3$.

3. A compound of claim 2 where Z is CH or N and X is $CH_3$ or $OCH_3$.

4. A compound of claim 3 where A is

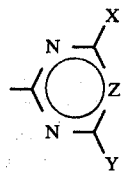

5. A compound of claim 4 where $R_1$ is H.

6. A compound of claim 5 where $R_2$ is H.

7. A compound of claim 6 where $R_3$, $R_4$ and $R_5$ are $C_1$–$C_3$ alkyl.

8. A compound selected from:

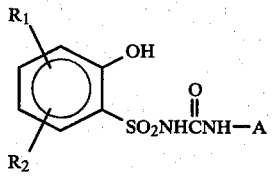

wherein $R_1$ is H, F, Cl, Br, $C_1$–$C_3$ alkyl, $NO_2$, $C_1$–$C_3$ alkoxy, $CF_3$ or

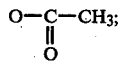

$R_2$ is H, $CH_3$ or Cl;

A is

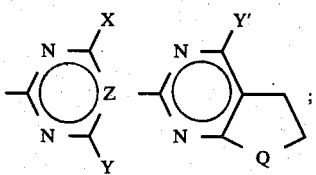

X is H, Cl, Br, $CH_3$, $CH_3CH_2$, $C_1$–$C_3$ alkoxy, $CF_3$, $CH_3S$ or $CH_3OCH_2$;

Y is $CH_3$ or $CH_3O$;

Z is N, CH, C—Cl, C—Br, C—CN, C—$CH_3$, —C—$CH_2CH_3$, C—$CH_2CH_2Cl$ or C—$CH_2CH$=$CH_2$;

Y' is H, $CH_3$, $OCH_3$ or Cl; and

Q is O or $CH_2$;

9. The compound of claim 8, 3,5-dichloro-N-[(4,6-dimethoxypyrimidin-2-yl)aminocarbonyl]-2-hydroxybenzenesulfonamide.

10. The compound of claim 8, 3,5-dichloro-2-hydroxy-N-[(4-methoxy-6-methyl-pyrimidin-2-yl)aminocarbonyl]benzenesulfonamide.

11. A composition for the control of undesirable vegetation consisting essentially of a compound of claim 1 and at least one of (a) a surface-active agent and (b) a solid or liquid diluent.

12. A composition for the control of undesirable vegetation consisting essentially of a compound of claim 2 and at least one of (a) a surface-active agent and (b) a solid or liquid diluent.

13. A composition for the control of undesirable vegetation consisting essentially of a compound of claim 3 and at least one of (a) a surface-active agent and (b) a solid or liquid diluent.

14. A composition for the control of undesirable vegetation consisting essentially of a compound of claim 4 and at least one of (a) a surface-active agent and (b) a solid or liquid diluent.

15. A composition for the control of undesirable vegetation consisting essentially of a compound of claim 5 and at least one of (a) a surface-active agent and (b) a solid or liquid diluent.

16. A composition for the control of undesirable vegetation consisting essentially of a compound of claim 6 and at least one of (a) a surface-active agent and (b) a solid or liquid diluent.

17. A method for the control of undesirable vegetation consisting of applying to the locus of such undesirable vegetation a herbicidally effective amount of a compound of claim 1.

18. A method for the control of undesirable vegetation comprising applying to the locus of such undesirable vegetation a herbicidally effective amount of a compound of claim 2.

19. A method for the control of undesirable vegetation comprising applying to the locus of such undesirable vegetation a herbicidally effective amount of a compound of claim 3.

20. A method for the control of undesirable vegetation comprising applying to the locus of such undesirable vegetation a herbicidally effective amount of a compound of claim 4.

21. A method for the control of undesirable vegetation comprising applying to the locus of such undesirable vegetation a herbicidally effective amount of the compound of claim 5.

22. A method for the control of undesirable vegetation comprising applying to the locus of such undesirable vegetation a herbicidally effective amount of the compound of claim 6.

* * * * *